United States Patent
Van Zyl et al.

(10) Patent No.: US 10,124,015 B2
(45) Date of Patent: Nov. 13, 2018

(54) SURFACTANT COMPOSITION

(75) Inventors: Johann Martin Van Zyl, Bellville (ZA); Johan Smith, Durbanville (ZA); Arthur Owen Hawtrey, Pinelands (ZA); Pieter Van Der Bijl, Goodwood (ZA)

(73) Assignee: Stellenbosch University, Stellenbosch (ZA)

( * ) Notice: Subject to any disclaimer, the term of this patent is extended or adjusted under 35 U.S.C. 154(b) by 712 days.

(21) Appl. No.: 13/581,442

(22) PCT Filed: Feb. 25, 2011

(86) PCT No.: PCT/IB2011/000394
§ 371 (c)(1),
(2), (4) Date: Aug. 27, 2012

(87) PCT Pub. No.: WO2011/104621
PCT Pub. Date: Sep. 1, 2011

(65) Prior Publication Data
US 2012/0321586 A1    Dec. 20, 2012

(30) Foreign Application Priority Data

Feb. 27, 2010 (ZA) .................................. 2009/07800
Dec. 10, 2010 (ZA) .................................. 2010/08905

(51) Int. Cl.
| | | |
|---|---|---|
| A61K 31/683 | (2006.01) | |
| A61K 38/02 | (2006.01) | |
| A61K 38/16 | (2006.01) | |
| A61K 9/00 | (2006.01) | |

(52) U.S. Cl.
CPC .......... *A61K 31/683* (2013.01); *A61K 9/0082* (2013.01); *A61K 38/02* (2013.01); *A61K 38/16* (2013.01)

(58) Field of Classification Search
None
See application file for complete search history.

(56) References Cited

U.S. PATENT DOCUMENTS

2002/0160515 A1    10/2002  Wolff et al.
2008/0069778 A1*   3/2008   Pargaonkar .................. 424/9.51

FOREIGN PATENT DOCUMENTS

WO      WO-07-885      *  2/2003
WO      2004060396 A2     7/2004

OTHER PUBLICATIONS

Agu et al.; "The Lung as a Route for Systemic Delivery of Thereapeutic Proteins and Peptides"; BioMed Central Ltd; Apr. 12, 2001; pp. 1-12.
Fujiwara et al.; "Artificial Surfactant Therapy in Hyaline-Membrane Disease"; The Lancet; Jan. 12, 1980; pp. 1-4.
Nicholas J. Gross; "Pulmonary Surfactant: Unanswered Questions"; Thorax 1995; pp. 325-327.
Mark Gumbleton; "Caveolae as Potential Macromolecule Trafficking Compartments within Alveolar Epithelium"; Elsevier Science; Apr. 3, 2001; pp. 281-300.
Haitsma et al.; "Exogenous Surfactant as a Drug Delivery Agent"; Elsevier Science; 2001; pp. 197-207.
Bijl et al.; "Human Vaginal Mucosa as a Model of Buccal Mucosa for In Vitro Permeability Studies: An Overview"; Current Drug Delivery; 2004; pp. 129-135.
Robert M. Kliegman, MD; "Neonatal Technology, Perinatal Survival, Social Consequences, and the Perinatal Paradox"; American Journal of Public Health; Jul. 1995; pp. 909-913.
Luke et al.; "The Changing Pattern of Infant Mortality in the US: The Role of Prenatal Factors and their Obstetrical Implications"; International Federation of Gynecology and Obstetrics; 1993; pp. 199-212.
John F. McGuire; Surfactant in the Middle Ear and Eustachian Tube: A Review; International Journal of Pediatric Otorhinolaryngology; 2002; pp. 1-15.
Petttit et al.; "The Development of Site-Specific Drug-Delivery Systems for Protein and Peptide Biopharmaceuticals"; Tibtech; Aug. 1998; pp. 343-349.

(Continued)

*Primary Examiner* — Celeste A Roney
(74) *Attorney, Agent, or Firm* — Ohlandt, Greeley, Ruggiero & Perle, L.L.P.

(57) ABSTRACT

The disclosure describes a composition comprising a lipidaceous carrier and a peptide complex formed from poly-L-lysine or a salt thereof; and either poly-L-glutamic acid or poly-L-aspartic acid, or a salt thereof. The composition can be used to prevent or treat a disease related to pulmonary surfactant dysfunction, such as hyaline membrane disease (HMD), respiratory distress syndrome (RDS), hydrocarbon poisoning, near-drowning, HIV/AIDS-related lung diseases, adult respiratory distress syndrome (ARDS) or acute lung injury (ALI), asthma, tuberculosis (TB) or severe acute respiratory syndrome (SARS). Alternatively, the composition can be used to increase the permeability of a pharmaceutical compound or composition across a membrane of a subject or to act as a carrier. The poly-L-lysine or salt thereof is longer than the poly-L-glutamic acid or poly-L-aspartic acid so that the complex that forms has a charge-neutralized region and a positively-charged region. The charge-neutralized region of the peptide complex interacts with the lipidaceous carrier, while the positively-charged region interacts with an aqueous and/or polar environment.

22 Claims, 12 Drawing Sheets

(56) References Cited

OTHER PUBLICATIONS

Schwartz et al.; "Effect of Surfactant on Morbidity, Mortality, and Resource Use in Newborn Infants Weighing 500 to 1500 g"; The New England Journal of Medicine; May 26, 1994; pp. 1476-1480.
Stolz et al.; "Restricting Access to Neonatal Intensive Care: Effect on Mortality and Economic Savings"; Pediatrics: Official Journal of the American Academy of Pediatrics; 1998; 1-7.
Strayer et al.; "Surfactant as an Immunogen: Implications for Therapy of Respitory Distress Syndrome"; Acta Paediatr; 1992; pp. 446-447.
Venkitaraman, A.R. et al., Hydrophobic homopolymeric peptides enhance the biophysical activity of synthetic lung phospholipids and Physics of lipids, 1990, vol. 53, pp. 157-164.
Pilvat, A-M et al., "Phospholipid Bilayers as Biomembrane-like Barriers in Layer-by-layer polyelectrolyte films"; Langmuir 2007, vol. 23, pp. 8236-8242—Abstract.
Matsumura, H. et al., "Effect of amino acids, polypeptides and proteins on electrophoretic mobilities of phospholipid lipsomes", Colliods and Surfaces A: Physicochemical and Engineering Aspects, 1994 vol. 92, pp. 87-93.
Ciobanu, M et al., "Layersome: Developmemt and optimization of stable liposomes as drug delivery system", International Journal of Pharmaceutics 2007, vol. 344, pp. 154-157 Abstract, p. 154, second column, p. 155, first column, p. 156, second column.
Acosta, E.J. et al., "Restoring the activity of serum-inhibited bovine lung extract surfactant (BLES) using catonic additives", Biochimica et Biophysica Acta, Mar. 2010, vol. 1798, No. 3, pp. 489-497 (available online Jan. 20, 2010).
International Search Report dated Jun. 30, 2011 from PCT/IB2011/000394.
European Search Report dated Apr. 18, 2013 corresponding to European Patent App. No. 11 74 6932.0, 5 pp.

* cited by examiner

SURFACTANT COMPOSITION

FIELD OF THE DISCLOSURE

This disclosure relates to a surfactant composition and its uses for treating or preventing one or more diseases or conditions related to pulmonary surfactant dysfunction or deficiency, for enhancing membrane permeability or for acting as a drug carrier of pharmaceutical compounds for use in treating other diseases or conditions.

BACKGROUND TO THE DISCLOSURE

Pulmonary surfactants are found at the alveolar surface and are essential for breathing. They consist of a complex mixture of phospholipids (85%), neutral lipids (5%), and several specific surfactant proteins (5%) which reduce surface tension at the alveolar surface, allowing for rapid gaseous exchange. The unique spreading properties of the pulmonary surfactant reduce surface tension, thereby promoting lung expansion (also known as compliance) during inspiration, and preventing lung collapse during expiration.

Without surfactant, the air sacs or alveoli of the lungs collapse and are unable to absorb sufficient oxygen. This can manifest as an inhibition of gas exchange in the lungs, causing a condition known as hyaline membrane disease (HMD), also known as respiratory distress syndrome (RDS). This condition occurs most frequently in premature infants, but also often occurs in older children and adults. Older children and adults may present with a wide spectrum of lung conditions which include, but are not limited to, hydrocarbon (e.g. paraffin) poisoning, near-drowning, HIV/AIDS-related lung diseases, adult respiratory distress syndrome (ARDS) or acute lung injury (ALI), asthma, chronic obstructive pulmonary disease (COPD), tuberculosis (TB), and severe acute respiratory syndrome (SARS).

The observation that preterm infants with RDS suffer from an alveolar surface-active material deficiency led to the treatment of the condition with exogenous surfactant replacements, and various pulmonary surfactants are now commercially available, such as those listed below in Table 1. These include mammalian-derived or natural surfactants containing surfactant proteins and synthetic protein-free lipid mixtures:

TABLE 1

A selection of commercially available pulmonary surfactants

| Generic name | Brand name | Manufacturer |
| --- | --- | --- |
| Beractant | Survanta ® | Abbott Laboratories (USA) |
| Surfactant-TA | Surfacten ® | Tokoyo Tanabe (Japan) |
| Porcine surfactant | Curosurf ® | Chiesi Pharmaceuticals (Italy) |
| Calf pulmonary surfactant (CLSE) | Infasurf ® | Forest Laboratories (USA) |
| SF-RI 1 | Alveofact ® | Boehringer (Germany) |
| Artificial lung expanding compound (ALEC) | Pneumactant ® | Britannia Pharmaceuticals (UK) |
| Colfosceril palmitate hexadecanol, tyloxapol | Exosurf ® | Glaxo Wellcome Co (USA) |

Mammalian-derived surfactant, also referred to herein as native or natural pulmonary surfactant, consists mainly of phospholipids, the major phospholipid being dipalmitoyl phosphatidylcholine (DPPC). It also includes phosphatidyl glycerol (PG) and surfactant proteins (SP) A, B, C, and D. The formation of tubular myelin, which is the active in vivo extracellular form of native pulmonary surfactant, requires the presence of DPPC, PG, SP-A, SP-B, and calcium. SP-B and SP-C are believed to assist natural surfactants to manifest superior in vivo and in vitro surface behaviour (Dizon-Co et al 1994). Of the various protein components of the pulmonary surfactant, SP-B appears to have an essential function in maintaining alveolar expansion. Indeed, simply supplementing artificial phospholipids with hydrophobic SP-B and/or SP-C, whether from native or recombinant sources, has been shown to result in improved in vivo and in vitro function (Dizon-Co et al 1994; Ikegami and Jobe 1998; Davis et al 1998). The absence of SP-B has been shown to result in both a deficiency in SP-C as well as causing lethal respiratory failure in full term infants (Nogee et al 1993; Clark et al 1995).

Mammalian-derived surfactants have been available for many years, but are expensive and their therapeutic application has been focused upon use in HMD/RDS occurrence in premature infants. These surfactant formulations usually contain proteins derived from bovine or porcine sources and hence pose a potential risk for the transmission of animal-associated pathogens.

Initial synthetic protein-free lipid surfactants, such as Exosurf®, have demonstrated inferior performance both in animal experiments and in human infant trials, when compared to surfactant formulations containing protein (Grossman et al 1984; Cummings et al 1992; Halliday 1997; Ainsworth et al 2000). Later synthetic surfactants, such as Lucinactant (Surfaxin®, Discovery Laboratories, Philadelphia), containing sinapultide KL4 have demonstrated superior performance with regard to the risk of mortality, chronic lung disease and other morbidities associated with prematurity in infants having HMD/RDS or at risk of developing the condition. However, in two trials in which such protein-containing synthetic surfactants were compared with animal-derived surfactant extract, no statistical difference in death or chronic disease was noted (Cochrane Syst Review, 2007). Furthermore, Lucinactant is a gel at room temperature and must first be warmed before use for it to be in a liquid form. Lucinactant has not yet been approved by the FDA for treatment in neonatal HMD/RDS.

The efficacy of the currently commercially available preparations has been assessed both in animal models of RDS and in clinical trials involving human infants with the same condition. Overall, the available protein-free synthetic formulations demonstrate inferior performance in vivo compared to that of protein-containing natural formulations. However, the safety of surfactants containing foreign protein has been questioned. Further drawbacks of surfactant preparations derived from animal tissues include the complexity of the manufacturing and sterilization processes required. Reconstituted surfactants generally include added hydrophobic proteins, either isolated from animal tissues or obtained through recombinant techniques, or synthetic peptidic derivatives of such proteins. The properties and activity of the reconstituted surfactants therefore greatly depend not only upon the h composition of the phospholipid mixture but also upon the peptide/protein components.

There is therefore a need for a synthetic pulmonary surfactant composition which has surface properties equivalent to those of natural surfactant.

SUMMARY

According to a first embodiment of the disclosure, there is provided a composition comprising:

a lipidaceous carrier;

poly-L-lysine or a pharmaceutically acceptable salt thereof; and poly-L-glutamic acid or poly-L-aspartic acid or a pharmaceutically acceptable salt thereof.

The poly-L-lysine or pharmaceutically acceptable salt thereof and poly-L-glutamic acid, poly-L-aspartic acid or pharmaceutically acceptable salt thereof may form a peptide complex with one another.

The salt of poly-L-lysine may be poly-L-lysine.HBr, preferably having the formula (I) where n ranges from about 100 to about 135, from about 103 to about 135, or from about 103 to about 119:

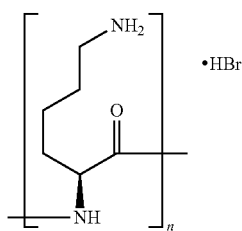

(I)

The salt of poly-L-glutamic acid may be poly-L-glutamic acid sodium salt, preferably having the formula (II) where x is at least 50, at least 68 or at least 86:

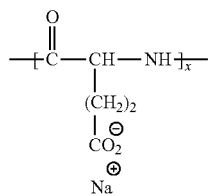

(II)

The poly-L-lysine chain or salt thereof may be longer than the poly-L-glutamic acid or poly-L-aspartic acid chains or salt thereof by at least 17 residues, by at least 50 residues or by at least 85 residues. For example, the poly-L-lysine chain or salt thereof may be longer by about 17 to 49 residues, about 50 to 85 residues or about 35 to 67 residues.

The lipidaceous carrier may comprise one or more of dipalmitoyl phosphatidylcholine (DPPC), phosphatidylglycerol (1,2-Diacyl-sn-glycero-3-phospho-[1-rac-glycerol) (PG), hexadecanol, cholesterol, tyloxapol or sodium chloride.

For example, the composition may comprise the following:

dipalmitoyl phosphatidylcholine (DPPC);
dipalmitoyl phosphatidylglycerol (PG);
hexadecanol;
tyloxapol;
poly-L-lysine.HBr;
poly-L-glutamic acid sodium salt; and
sodium chloride.

The composition may further comprise a pharmaceutically acceptable carrier.

The composition is typically used for preventing or treating a disease or condition related to pulmonary surfactant dysfunction or defiency, such as hyaline membrane disease (HMD), respiratory distress syndrome (RDS), hydrocarbon poisoning, near-drowning, HIV/AIDS-related lung diseases, adult respiratory distress syndrome (ARDS) or acute lung injury (ALI), asthma, obstructive pulmonary disease (COPD), tuberculosis (TB) or severe acute respiratory syndrome (SARS).

Alternatively, the composition may be used for increasing the permeability of a pharmaceutical compound or composition across a membrane of a subject or act as a drug carrier. The pharmaceutical compound, composition or drug may be, but not limited to an anti-cancer agent, anti-inflammatory, immunosuppressive agent, antidiuretic agent, carrier peptide, microbicidal peptide, ACTH suppressor, cortisol analogue or hormone replacement therapy agent, and may be administered concurrently with the composition described above or may be included therein.

The composition may be suitable for administration by inhalation, intubation or direct pulmonary administration.

According to a further embodiment of the disclosure, there is provided a method for manufacturing the composition described above, the method comprising the steps of:

mixing dipalmitoyl phosphatidylcholine (DPPC), hexadecanol, and phosphatidylglycerol (PG) in an organic solvent;

removing the organic solvent and obtaining a phospholipid film;

mixing, in an aqueous solution, poly-L-lysine or a pharmaceutically acceptable salt thereof and poly-L-glutamic acid or poly-L-aspartic acid, or a pharmaceutically acceptable salt thereof, and obtaining a peptide complex;

adding the peptide complex to the phospholipid film;
agitating the mixture, and
adding tyloxapol.

According to a further embodiment of the disclosure, there is provided the use of a composition as described above in the manufacture of a medicament for use in a method of preventing or treating a condition related to pulmonary surfactant dysfunction or defiency in a subject, the method comprising administering to the subject an effective dose of the composition.

According to a further embodiment of the disclosure, there is provided a method of treating or preventing a condition related to pulmonary surfactant dysfunction or deficiency in a patient, which comprises administering to a subject an effective dose of the composition described above.

According to a further embodiment of the disclosure, there is provided a method of administering a pharmaceutical compound or composition to a subject, which comprises the step of administering to the subject an effective amount of the pharmaceutical compound or composition together with an effective amount of the composition described above.

DETAILED DESCRIPTION OF THE PREFERRED EMBODIMENT

Figure 1:
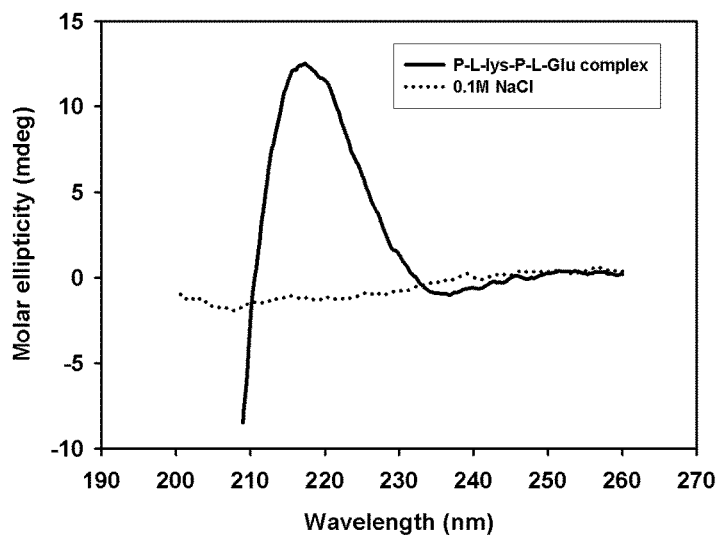
FIG. 1 is a graph of Molar ellipticity (mdeg) versus wavelength (nm) showing the circular dicroism (CD) spectrum of the poly-L-lysine, poly-L-glutamic acid complex as described in Example 1.

A composition comprising a lipidaceous carrier and a peptide complex formed from two polypeptides is described herein. The first polypeptide is poly-L-lysine or a pharmaceutically acceptable salt thereof; and the second polypeptide is either poly-L-glutamic acid or poly-L-aspartic acid, or a pharmaceutically acceptable salt thereof.

The composition is used to temporarily substitute for natural pulmonary surfactant in a mammalian lung where such natural pulmonary surfactant is absent, dysfunctional or present in low concentration. Unlike other surfactant compositions, the present composition does not contain any proteins derived from non-human sources.

The composition can be used to prevent or treat a condition related to pulmonary surfactant dysfunction, such as hyaline membrane disease (HMD), respiratory distress syndrome (RDS), hydrocarbon poisoning, near-drowning, HIV/AIDS-related lung diseases, adult respiratory distress syndrome (ARDS), asthma, chronic obstructive pulmonary disease (COPD), tuberculosis (TB) or severe acute respiratory syndrome (SARS). Alternatively, the composition can be used to increase the permeability of a pharmaceutical compound or composition across a membrane of a subject or act as drug carrier. The pharmaceutical compound, composition or drug can be, but is not limited to, an anti-cancer agent, anti-inflammatory, immunosuppressive agent, antidiuretic agent, carrier peptide, microbicidal peptide, ACTH suppressor, cortisol analogue or hormone replacement therapy agent, and can be administered as a separate formulation but concurrently with the composition described above or may even be included as part of the same composition. The composition can be administered endotracheally into the lungs of a mammal to temporarily substitute for natural pulmonary surfactant and to create a film on the alveolar interfacial surfaces and reduce surface tension. Expansion of the alveolar spaces is thereby facilitated. Alternatively, the composition can be administered to a subject by inhalation, intubation or direct pulmonary administration.

The poly-L-lysine chain or salt thereof is generally longer than the poly-L-glutamic acid or poly-L-aspartic acid chain or salt thereof by at least 17 residues, by at least 35 residues, by at least 50 residues or by at least 85 residues. For example, the poly-L-lysine chain or salt thereof may be longer by about 17 to 49 residues, about 50 to 85 residues or about 35 to 67 residues. As the poly-L-lysine is predominantly positively charged and the poly-L-glutamic acid is predominantly negatively charged, the peptide complex that forms between these two polypeptides has an essentially charge-neutralised region and an essentially positively-charged region. The charge-neutralised region of the peptide complex is capable of interacting with the lipidaceous carrier, while the positively-charged region is available to interact with an aqueous and/or polar environment.

The ratio of the first polypeptide to the second polypeptide is about 1:0.3 (w/w); and the ratio of the peptide complex to the lipidaceous carrier is about 3:100 (w/w), and more particularly is 3.9:100 (w/w).

The poly-L-lysine $((Lys)_n)$ is typically in the form of poly-L-lysine.HBr, having the formula (I) where n ranges from about 100 to about 135, more preferably from about 103 to about 135, and even more preferably from about 103 to about 119.

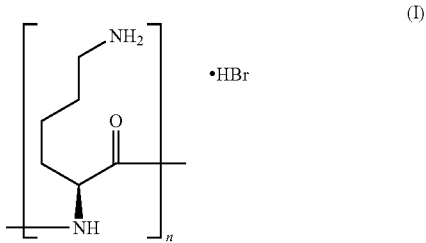

(I)

The poly-L-glutamic acid is typically in the form of poly-L-glutamic acid sodium salt, having the formula (II) where x is at least 50, preferably at least 68 or even more preferably at least 86.

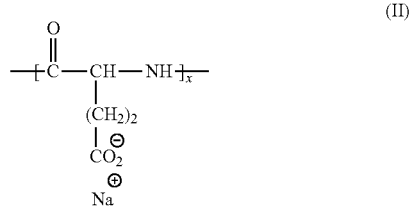

(II)

The lipidaceous carrier can include one or more of dipalmitoyl phosphatidylcholine (DPPC), phosphatidylglycerol (PG), hexadecanol, cholesterol, tyloxapol or sodium chloride. The ratio of the DPPC, hexadecanol and the PG can be about 10:1.1:1 (w/w).

The composition can optionally include cholesterol; for example in concentrations from about 3 mg/ml to about 4.8 mg/ml, so as to comprise about 5 to about 8% (w/w) of the composition.

One example of a suitable embodiment of the disclosure is a composition which comprises:

| | |
|---|---|
| dipalmitoyl phosphatidylcholine (DPPC) | 60 mg/ml; |
| phosphatidylglycerol (PG) | 6 mg/ml; |
| hexadecanol | 6.7 mg/ml; |
| tyloxapol | 1 mg/ml; |
| poly-L-lysine•HBr | 1.98 mg/ml; |
| poly-L-glutamic acid sodium salt | 0.613 mg/ml; and |
| sodium chloride | 100 mM. |

As used herein, the term "lipidaceous carrier" means a mixture of phospholipids and optionally other lipid components, for example neutral lipids such as triacylglycerols, free fatty acids and/or cholesterol.

As used herein, the terms "comprising predominantly of" or "essentially" mean to comprise mainly of. For example, a region having a predominantly or essentially positive charge means that the overall (or net) charge of the region is positive.

As used herein, the term dipalmitoylphosphatidyl choline refers to 1,2-Dihexadecanoyl-sn-glycero-3-phosphocholine.

As used herein, the term phosphatidylglycerol refers to 1,2-Diacyl-sn-glycero-3-phospho[1-rac-glycerol].

As used herein, an effective dose for treating a condition is an amount that is sufficient to ameliorate, or in some manner reduce the symptoms associated with the disease. The amount will depend on the kind and the severity of the condition and the characteristics (weight, sex, age) of the subject.

EXAMPLES

The disclosure is described below with reference to a particular embodiment of the disclosure, wherein the composition comprises a lipidaceous carrier which includes a phospholipid mixture made up of dipalmitoyl phosphatidylcholine (DPPC); hexadecanol; phosphatidylglycerol (PG) in the ratio of 10:1.1:1 (w/w), and a peptide complex formed from a first polypeptide in the form of poly-L-lysine.HBr (having about 100-135 amino acid residues) and a second polypeptide in the form of poly-L-glutamic acid sodium salt (having about 86 amino acid residues). The applicant has used the term "Synsurf" to refer to the pulmonary surfactant composition of the disclosure.

The process for preparing the surfactant composition includes first preparing the lipidaceous carrier by mixing the DPPC, hexadecanol, and PG in an organic solvent, such as chloroform, before removing the organic solvent by rotary evaporation at 35° C. under reduced pressure to obtaining a phospholipid film. The poly-L-lysine and poly-L-glutamic acid polypeptides are then allowed to complex with one another by mixing at 37° C. in aqueous solution containing sodium chloride before being added to the phospholipid film. The peptide complex and phospholipid film mixture is then sonicated under substantially mild conditions.
XXXXXXXXXXXXXXXXXXXXXXXXXXXXXXXXXXXX In the examples set out below, the pulmonary surfactant composition of the disclosure is prepared and used in in vivo animal trials and in in vitro permeability studies using animal and human tissue specimens. Example 1 sets out how the pulmonary surfactant composition is prepared, together with biochemical analysis thereof. Example 2 sets out the results obtained when the pulmonary surfactant composition was used as early pulmonary surfactant treatment for respiratory distress syndrome in preterm lambs as compared to the commercially available Survanta®. Example 3 sets out the results obtained when the pulmonary surfactant composition was used in a randomised trial to treat respiratory distress syndrome in preterm lambs as compared to the commercially available Curosurf®. Example 4 sets out the results of permeability studies using the pulmonary surfactant composition to diffuse various agents through human and animal tissue specimens.

Example 1: Preparation and Analysis of Synsurf

Materials 1,2 Dihexadecanoyl-sn-glycero-3-phosphocholine (DPPC) and 1,2 Diacyl-sn-glycero-3phospho-[1-rac-glycerol] (PG) were obtained from Avanti Polar Lipids (Alabaster, Ala.), cetyl alcohol, tyloxapol, poly-L-lysine (HEW salt Sigma P7890) and poly-L-glutamic acid (Sodium salt Sigma P4636) were purchased from the Sigma Chemical Company (St. Louis Mo.). Phospholipid purity was verified by thin-layer chromatography (TLC). Sterile water for injection was used in the preparation of pulmonary surfactant. Chloroform used was HPLC grade (Merck, Darmstadt).

Methods

Pulmonary Surfactant Preparations

The composition of the disclosure, hereinafter referred to as "Synsurf", was prepared by mixing DPPC (450 mg), hexadecanol (49.995 mg) and PG (45 mg) (in approximately a 10:1.1:1 ratio (w/w)) in 5 ml chloroform. The organic solvent was then removed by rotary evaporation and the mixture was dried under a continuous stream of nitrogen at room temperature. Poly-L-lysine (24.8 kDa) (47.52 mg, 119 residues) was mixed with poly-L-glutamate (10.2 kDa) (14.7 mg, 86 residues) and incubated at 37° C. in 100 mM NaCl for 30 mins. The complex was prepared in such a manner as to be positively charged through having an excess of poly-L-lysine residues. The dried phospholipid film was then hydrated with the polymer mixture (3.9%) by weight of the phospholipid concentration), and gently mixed in the presence of glass beads. A ultrasonicater fitted with a microtip was then used to sonicate the mixture on ice under a stream of nitrogen (power of 20 watts for 7×13 seconds; 60 second intervals). Hereafter, 24 mg of tyloxapol was added to the preparation and the tube was sealed under nitrogen before use.

A generic Exosurf (GE) pulmonary surfactant was also prepared in a similar fashion as described above and consisted of three components: DPPC/hexadecanol/tyloxapol (13.5:1.5:1) in 100 mM NaCl. The dose of Synsurf and GE used in animal experiments was 100 mg/kg.

Liquid Surface Tension Measurements

The surface tension properties of the Synsurf and GE were measured with a CAHN 322 Dynamic Contact Angle Analyser. A platform speed of 100 microns/sec was used with a data collection rate of 1 per sec. A glass plate (22 mm×22 mm×0.15 mm) was used as the force sensor. Immersion was in a 25 ml glass beaker containing 12 ml of the sample and single cycles were recorded at 25° C. Five sets of triplicate analyses were done.

Circular Dichroism Spectroscopy

Analysis of the secondary structure of the poly-L-lys-poly-L-glutamic acid complex was carried out at room temperature with a Jasco-810 spectropolarimeter. The polymer complex was diluted with 100 mM NaCl giving final peptide concentrations of 6.6 µM p-lysine and 3.2 µM p-glutamic acid respectively.

Results

Liquid Surface Tension Measurements

DPPC is an uncharged molecule with a solid-to-liquid-crystal transition temperature of 41.6° C. (Van Golde et al., 1988). It therefore does not spread well at an air-liquid interface at normal body temperature. To aid spreading of the DPPC in Synsurf during experiments in the pulmonary surfactant depleted rabbit model, phosphtidylglycerol (PG) was included in the formulation. The negatively charged PG molecule stabilises a phospholipid emulsion in water and facilitates the disruption of liposomes touching an air-liquid interface (Enhorning, 1984).

The comparative analyses of surface tension of Synsurf and GE preparations showed no statistically significant differences, and values of 37.7 mN/m and 37.6 mN/m were noted for the Synsurf and GE formulations, respectively. Although surface tension measurements depend upon the technique applied, the present data measured under dynamic conditions are in agreement with poor surface tension function measured in the absence of SP-B/C (Notter, 1983).

Circular Dichroism Spectroscopy

Poly-L-lysine can exist in a variety of conformations depending on the degree of ionization of the amino groups in the side chains, temperature and salt concentration. When the circular dichroism (CD) spectrum of the poly-L-lysine, poly-L-glutamic acid complex was examined, it showed a maximum at 218 nm, indicative thereof that the mixture exists in the native random coil conformation (FIG. 1). This is in accordance with the findings of Chittchang and co-workers who found that the random coil is the native secondary structure of polylysine (Chittchang et. al., 2002). Although hydrophobicity of poly-L-lysine significantly increases in the order: random coil<α-helix<β-sheet conformers (Gray et al. 1994), complexes of poly-L-lysine, poly-L-glutamic acid have a degree of hydrophobicity, as conjugates of polylysine electrostatically bind to DNA and make good cell transfecting agents (Larson et. al. 2004). Moreover, poly-L-lysine adopts a β-sheet conformation from the random coil during interaction with phospholipids (Fukushima et. al. 1994). However, the random coil (disordered state) of a polymer mixture tends to favour the exposure of the basic charged surface groups on the lysine side chains whereby the peptide may interact flexibly with other molecules to perform a functional role in cell membranes. The overall effect may then be electrostatic binding to phospholipids monolayers (Carrier et. al., 1985). With regards to SP-B, the α-helical and β-sheet secondary structure is proposed to penetrate into the lipid acyl chains of the phospholipid membrane lining in alveolar walls, thus providing stability and preventing atelectatic collapse (Whitsett et al., 2002).

The charged amino groups of poly-L-lysine in the present preparation may also interact with the phospholipid bilayer, mimicking one or more structural and/or functional properties of SP-B. Alternatively, as positive charges are believed to be important for maintaining the structure and function of SP-C(Creuwels et al., 1995), it may be argued that the overall positive character of poly-L-lysine residues in Synsurf might mimic SP-C structural and/or functional properties.

Example 2: Dead Space Capnometry, Lung Mechanics and Blood Gas Analyses after Synthetic Pulmonary Surfactant Replacement Therapy in a Pulmonary Surfactant-Depleted Model The low concentrations of pulmonary surfactant proteins in natural pulmonary surfactants give them the edge in terms of improvement in systemic oxygenation, lung mechanics and outcome in infants with respiratory distress syndrome (RDS), above that achieved by synthetic protein-free products. Although improvement of systemic oxygenation after pulmonary surfactant replacement therapy (SRT) is due to recruitment of collapsed alveoli or stabilization and hyperinflation of recruited lung compartments, decreased dead space, improvement in lung mechanics or decreased shunting, the exact mechanism remains uncertain and controversial. In laboratory animals, repeated lavage elevates alveolar and physiological dead space, associated with a decrease in oxygenation. Subsequent natural SRT improves oxygenation without restoring the lung to its prelavage condition.

The following example describes a randomized trial in which the composition of the disclosure (Synsurf) was evaluated against two other synthetic pulmonary surfactants, in an adult New Zealand White Rabbit model, rendered pulmonary surfactant-deficient by repeated saline lavage according to the procedures of Lachmann et al. (1982).

Methods

Surfactants Used

Synsurf, prepared according to the procedure set out in Example 1.

GE- Generic Exosurf (prepared by a standard method, as set out in Example 1.)

GE+ $Ca^{2+}$— Generic Exosurf+$Ca^{2+}$

Determination of In Vivo Pulmonary Surfactant Activity

Animal care and experimental procedures were performed with approval from the Faculty of Health Sciences Research Committee at Stellenbosch University. Adult New Zealand White rabbits were used as a model of pulmonary surfactant depletion. A tracheotomy was performed under local anesthesia and an uncuffed tube inserted into the trachea. Mechanical ventilation using standardized settings was commenced under continuous intravenous anesthesia with pentobarbital. Paralysis was achieved with pancuronium bromide. Repeated lavage was performed using 20 ml/kg warm saline (~37° C.) via the endotracheal tube for each washing. Lavage end-points included a decrease in arterial oxygen tension ($PaO_2$) below 11 kPa (Fraction of inspiratory oxygen concentration; $FiO_2$ 1.0) and a decrease in dynamic respiratory compliance (Cdyn) by 40% or more. Five minutes after lavage, animals were randomized into three groups. Pulmonary surfactant preparations were administered via the endotracheal tube (DPPC concentration 100 mg/kg). The $FiO_2$, expiratory tidal volumes, respiratory rate and the positive end-expiratory pressure (PEEP) were kept constant throughout the study. Pulmonary function was measured with a $CO_2$SMO Plus respiratory profile monitor (Novametrix Medical Systems Inc.). Partial pressure of end-tidal carbon dioxide tension ($PET_{CO2}$) was measured by mainstream infrared absorption. By using the arterial $CO_2$ tension ($PaCO_2$) and volume measurements, the anatomic deadspace, alveolar deadspace (Vdalv), physiological (phys) deadspace and deadspace/tidal volume (Vt) ratio were determined. Blood gases, volume measurements and Cdyn were measured before and after lavage, and at 30, 60, 90, 120, 180, 240 and 300 min after pulmonary surfactant replacement therapy. The study lasted 5 hours before euthanasia of animals by a lethal intra-arterial injection of 15% potassium chloride.

Chest Radiography

Antero-posterior chest radiographs were taken prior to lavage, immediately prior to randomization and at the end of the study. Changes in lung fields were assessed in a blinded manner in regard to whether the radiographic opacification following lavage (atelectasis) resolved (better), remained unchanged (similar) or deteriorated (worse).

Statistical Methods

The variables measured for groups at the preset time points were compared using unpaired t tests. For continuous variables measured over time, a linear regression of the variables over time by least-squares analysis was used to compare groups by differences in the initial responses to pulmonary surfactant (y-intercepts) and change over time (slopes). Data is expressed as mean±SD. A p-value<0.05 was taken as significant.

Results

Figure 2:
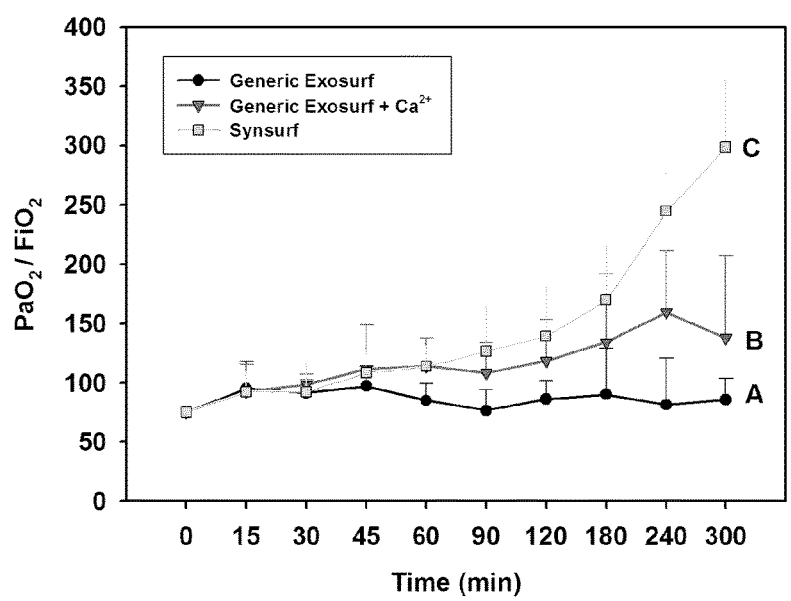
FIG. 2: is a graph of $PaO_2/FiO_2$ versus Time (min) showing the oxygenation profile of rabbits treated with the composition of Example 1, generic exosurf (GE), or GE and $Ca^{2+}$ as described in Example 2, p: $=6.6 \times 10^{-6}$ for datasets A and C; p: $=0.0002$ for datasets C and B, and p: $=0.04$ for datasets A and B.
Figure 3:
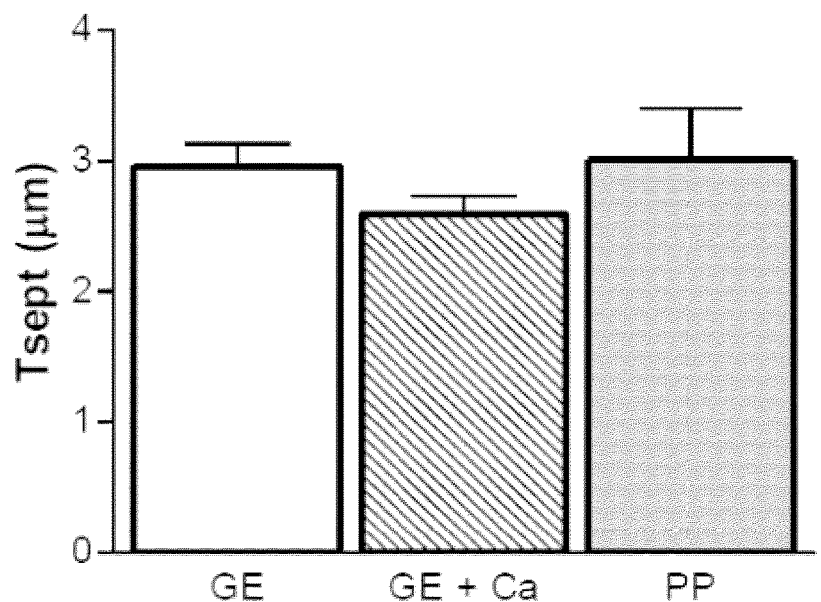
FIG. 3: is a bar graph showing the effect of pulmonary surfactant replacement on septal thickness (Tsept) (μm) in n=6 lambs treated with GE, GE and $Ca^{2+}$ (GE+Ca), or the composition of the disclosure as described in Example 2.

The Vdalv, Vd/Vt ratio and $PaCO_2$-$ETCO_2$ difference (delta) increased significantly, while the $PaO_2$ and Cdyn, decreased significantly following repeated lavage (Table 2). In the group as a whole, pulmonary surfactant instillation did not restore any of the measured variables to pre-lavage conditions (Table 3). Significantly better oxygenation ($PaO_2$ values) was documented in the Synsurf group in comparison to the other two groups (FIG. 2). The Synsurf group of animals had significantly lower $PaCO_2$-$ETCO_2$ differences than the GE group at 300 min (data not shown). Overall, a negative correlation existed between the a/A ratio and Vd/Vt ratio (r=0.72) and a significant positive correlation between the delta $PaCO_2$-$ETCO_2$ and Vd/Vt ratio (r=0.8). Despite manifesting better oxygenation, animals in the Synsurf group manifested poorer correlations between $PaO_2$ and delta $PaCO_2$-$ETCO_2$ and $PaO_2$ and Vd/Vt ratio in comparison to the other groups. All of the rabbits in the three study groups survived until the end of the study period. CXR improved in 3/4 animals in the Synsurf group in comparison to 1/4 in GE+$Ca2^+$ group and 2/4 in the GE group (Table 4). Synthetic pulmonary surfactant replacement did not restore the lung to its pre-lavage condition.

TABLE 2

Pe-lavage vs Post-lavage (time point 0) (mean ± SD)

| Variables | ALL n = 12 | GE n = 4 | GE + Ca2+ n = 4 | Synsurf n = 4 |
|---|---|---|---|---|
| Pre-PaO$_2$/FiO$_2$ | 67.5 (2.2) | 68.1 (2.3) | 67.9 (3.2) | 66.6 (1.2) |
| Post-PaO$_2$/FiO$_2$ | 7.2 (2) | 7.1 (2.1) | 6.7 (2.4) | 7.7 (1.9) |
| Pre PaCO$_2$—ETCO$_2$ (kPa) | 1.31 (1.12) | 1.62 (0.89) | 1 (1.09) | 1.25 (1.55) |
| Post PaCO$_2$—ETCO$_2$ (kPa) | 3.1 (1.5) | 3 (1.28) | 3.55 (1.66) | 2.77 (1.8) |
| Pre Vd/Vt | 0.61 (0.08) | 0.61 (0.01) | 0.58 (0.08) | 0.65 (0.07) |
| Post Vd/Vt | 0.78 (0.05) | 0.78 (0.0) | 0.79 (0.05) | 0.77 (0.08) |
| Pre Vd alv (ml) | 11.3 (3.67) | 10.7 (3.5) | 10.7 (2.5) | 12.5 (5.19) |
| Post Vd alv (ml) | 14.5 (2.9) | 12.7 (2.2) | 16.7 (1.25) | 14.2 (3.8) |
| Pre Cdyn ml/cmH$_2$O/kg | 2.91 (0.5) | 2.8 (0.3) | 3.02 (0.74) | 2.85 (0.46) |
| Post Cdyn ml/cmH$_2$O/kg | 1.42 (0.22) | 1.36 (0.21) | 1.45 (0.25) | 1.45 (0.26) |

TABLE 3

Pre-lavage variables vs variables at 300 min (study endpoint) for ALL (mean ± SD)

| Variable | MEAN | SD | ANOVA |
|---|---|---|---|
| Pre PaO$_2$/FiO$_2$ | 67.5 | 2.2 | P < 0.0005 |
| 300 min PaO$_2$/FiO$_2$ | 20.8 | 13.4 | |
| Pre PaCO$_2$—ETCO2 (kPa) | 1.31 | 1.12 | P = ns (0.08) |
| 300 min PaCO$_2$—ETCO$_2$ (kPa) | 2 | 0.77 | |
| Pre Vd/Vt | 0.61 | 0.08 | P < 0.003 |
| 300 Vd/Vt | 0.73 | 0.06 | |
| Pre Vd alv (ml) | 11.3 | 3.6 | P = ns |
| 300 min Vd alv (ml) | 12.4 | 2.8 | |
| Pre Cdyn (ml/cmH$_2$O/kg) | 2.9 | 0.50 | P < 0.002 |
| 300 min Cdyn (ml/cmH$_2$O/kg) | 1.4 | 0.24 | |

TABLE 4

Chest radiography changes

| Change: Pre-lavage vs end of study | GE N = 4 | GE + Ca2+ N = 4 | Synsurf N = 4 |
|---|---|---|---|
| Better | 2 | 1 | 3 |
| Similar | 1 | 3 | |
| Worse | 1 | | 1 |

Discussion

All animals experienced deterioration in Vd/Vt ratio (physiological deadspace). Systemic oxygenation was markedly superior over time in the Synsurf-treated animals. A lesser degree of intrapulmonary right-to-left-shunting as reflected by the intra group differences in $PaCO_2$-$ETCO_2$ values, may explain this finding. Furthermore, although it is known that $Ca^{2+}$ can stabilize membranes and films of polar phospholipids at the air-liquid interface, our experiments show that oxygenation status of the animals that received GE+$Ca^{2+}$ was inferior to that of the animals that was treated with Synsurf. Systemic oxygenation was therefore significantly improved in animals treated with Synsurf. This improvement was significantly superior to that of generic "Exosurf". This improvement might be due to a lower degree of intrapulmonary shunting as reflected by the $PaCO_2$-endtidal $CO_2$ difference in this group (Table 2).

Example 3: Early Rescue Pulmonary Surfactant Treatment for Respiratory Distress Syndrome in Preterm Lambs: Comparison of Synsurf with Bovine-Derived Survanta®

Example 3 is a randomized trial in which Synsurf, was evaluated against commercially available bovine-derived pulmonary surfactant Survanta® (ABBOTT Lab), with respect to systemic oxygenation and lung mechanics during instillation in preterm lambs 30 min after birth.

Methods

Pulmonary Surfactants Used

Synsurf, prepared according to the procedure set out in Example 1.

Survanta®

Determination of In Vivo Pulmonary Surfactant Activity

Animal care and experimental procedures were performed under approval from the Faculty of Health Sciences Committee for Human Research of Stellenbosch University. Twelve pregnant Dorper ewes were preanesthetized, intubated and received halothane anaesthesia and intermittent positive pressure ventilation. A cesarean section was performed on the time-dated pregnant ewes at 126-129 days gestational age (normal gestation 145-150 days). The fetal head was exposed, a tracheotomy performed and an uncuffed 4 or 4.5 mm endotracheal tube placed. Ten to 20 ml of fetal lung fluid was sampled to determine lung maturity. The umbilical cord was cut; animals were then delivered, dried, and weighed, sedated and paralyzed. Ventilation with the same ventilation style to achieve a tidal volume of 9-11 ml/kg was started. Ventilator settings were held constant throughout the study at a $FiO_2$ of 1.0, rate 40 bpm, Ti 0.70 sec and Peep 4 cm $H_2O$. Lambs were assigned into one of two groups (n=6 lambs/group) within 30 minutes of delivery. Two pulmonary surfactants were tested (concentration 100 mg/kg): Group A received Synsurf and Group B, Survanta®. Pulmonary surfactant was administered as early rescue treatment, within 35 minutes of delivery. The measurements of physiological variables, blood gases and in vivo lung mechanics was measured at 30, 45, 60, 90, 120, 180, 240 and 300 min after surfactant replacement (SR). After 5 hours, all live animals were killed. Lungs of all the animals were removed for histology and morphometry.

Histology

Lungs were inflated with air at 25 cm $H_2O$ static pressure, fixed with 10% buffered formalin. Samples taken were stained with hematoxylin and eosin stain (H&E) and examined by light microscopy under 100× magnification.

Results

Pre-treatment parameters for both groups are given in Table 5. There were no statistically significant differences between the groups. All the lambs were severely pulmonary surfactant deficient, as the mean lamellar body count, a reflection of total lung phospholipids, at delivery was negligible.

TABLE 5

Pre-treatment parameters Synsurf versus Survanta ® (Mean SD)

| Variables | Synsurf: n = 6 | Survanta ®: n = 6 |
|---|---|---|
| Body weight (kg) | 2.73 (0.55) | 2.38 (0.74) |
| Gestational age (days) | 128.5 (0.54) | 128 (1) |
| Male/Female | 2/4 | 1/5 |
| Lamellar body count/ml | 4666 (3386) | 6500 (3271) |
| Tracheal fluid (ml/kg) | 6.5 (2.6) | 7.9 (2.5) |
| Minute ventilation (ml/min/kg) | 347 (44.6) | 351 (30.3) |
| Tidal volume (TV/kg) | 9.7 (0.8) | 9.7 (0.6) |
| Mean pulmonary airway pressure (cm $H_2O$) | 14.8 (2.6) | 13.8 (0.98) |
| Cdyn (ml/cm $H_2O$/kg) | 0.29 (0.08) | 0.33 (0.65) |
| $VCO_2$/kg ($CO_2$ production per kg body weight) | 1.38 (0.5) | 1.08 (0.88) |
| $C_{20}$/C (Dynamic compliance over the last 20% of breath as a % of total breath Cdyn) | 1.3 (0.37) | 1.15 (0.23) |
| Mean Blood pressure (mmHg) | 55.6 (14.3) | 54.8 (3.7) |
| Pulse (per min) | 170 (34.3) | 165 (19.6) |
| Central venous pressure (cm $H_2O$) | 6 (3) | 5.2 (0.9) |
| Rectal temp (° C.) | 36.9 (0.5) | 36.7 (0.56) |
| $PaO_2$/$FiO_2$ | 36.8 (20.3) | 26.6 (10.7) |
| $PaCO_2$ (kPa) | 7.8 (1.9) | 10 (1.9) |
| pH | 7.30 (0.06) | 7.22 (0.09) |
| $CO_2$ total (mmol/L) | 31.1 (3.5) | 32.9 (1.4) |
| Base deficit | 1.8 (1.1) | 1.2 (3.1) |
| Oxygenation index (cm $H_2O$/kPa) | 7.3 (4.4) | 7.8 (2.9) |
| Birth-surf interval (min) | 29.8 (2) | 28.8 (3.6) |

Figure 4:
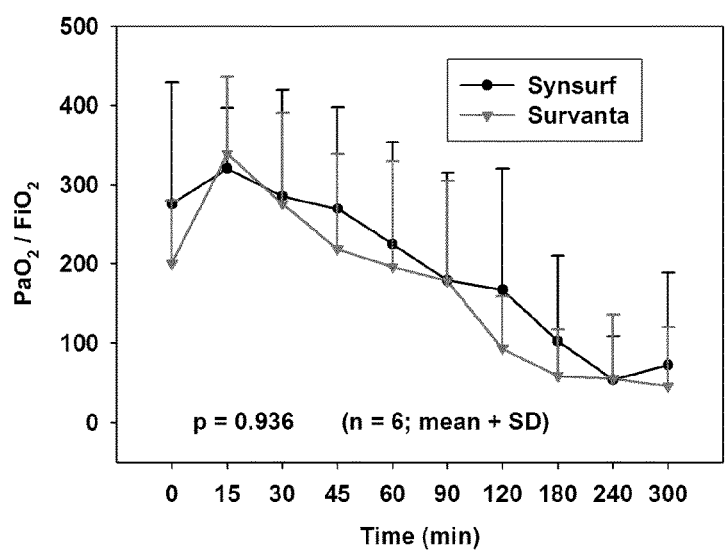
FIG. 4: is a graph of $PaO_2/FiO_2$ versus time (min) showing the mean systemic oxygenation profile of n=6 lambs treated with the composition of the disclosure and Survanta®, as described in Example 3, p: =0.936.
Figure 5:
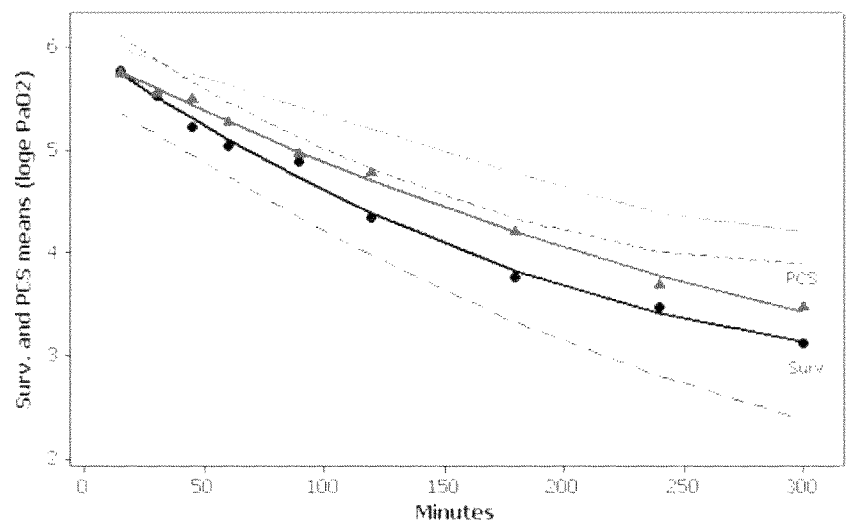
FIG. 5: is a graph of $\log_e PaO_2$ versus Time (min) showing the observed means and means of fitted curves of n=6 lambs treated with the composition of the disclosure and Survanta®, as described in Example 3.

Within 15 minutes of pulmonary surfactant instillation, animals in the Synsurf group and Survanta group experienced an increase in $PaO_2$/$FiO_2$ ratio (p=ns). Hereafter, however, both groups experienced significant deterioration in systemic oxygenation ($PaO_2$/$FiO_2$ ratio) over the study period (FIGS. 4 and 5). Within 45-90 min after pulmonary surfactant instillation, systemic oxygenation gradually deteriorated to below that of the baseline values with no real differences between the groups at any time-point (FIGS. 4 and 5) except for higher $PaO_2$ values in Group A (Synsurf) at 300 min (p<0.05).

Arterial blood gases ($PaCO_2$, pH), ventilator indices and haemodynamic variables were similar in both groups for the 5-hour study period. Four of the 6 animals in the Synsurf group survived to the end of the study. In this group, 3 animals developed a pneumothorax, at 45 min, 90-120 min and 180 min, respectively. All of the animals in the Survanta group survived until the end of the study and none developed a pneumothorax (Survival: Synsurf vs Survanta; p=ns).

Figure 6:
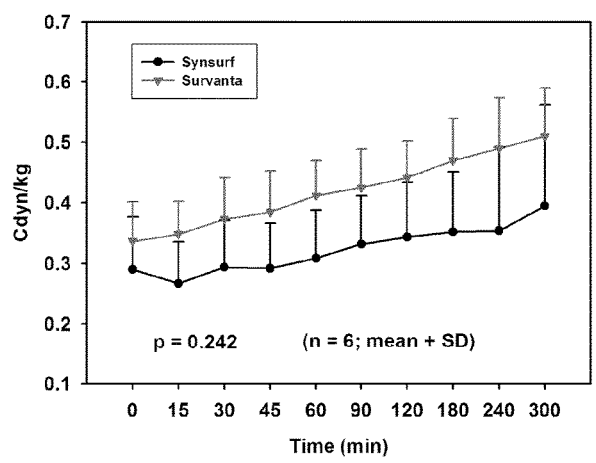
FIG. 6: is a graph of respiratory compliance (Cdyn/kg) over Time (min) in the n=6 lambs treated with the composition of the disclosure and Survanta® as described in Example 3, p=0.242.
Figure 7:
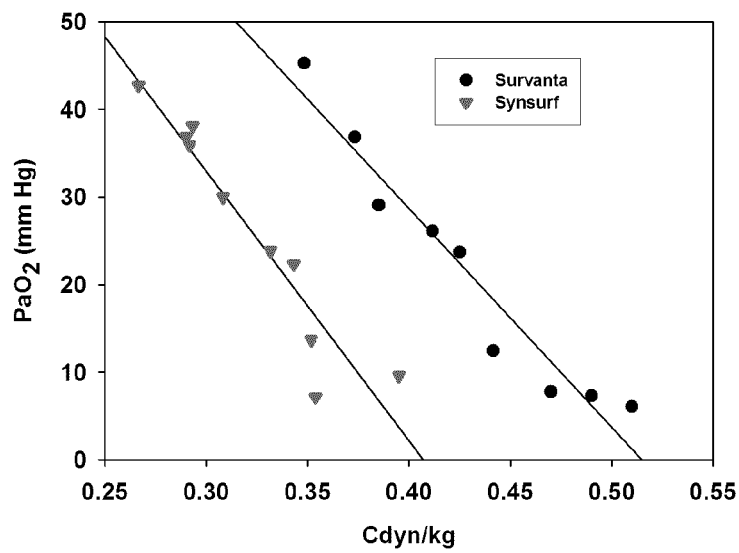
FIG. 7: is a regression plot of systemic oxygenation ($PaO_2$ in mm Hg) versus dynamic respiratory compliance (Cdyn/kg) in the n=6 lambs treated with the composition of the disclosure and Survanta® as described in Example 3.
Figure 8:
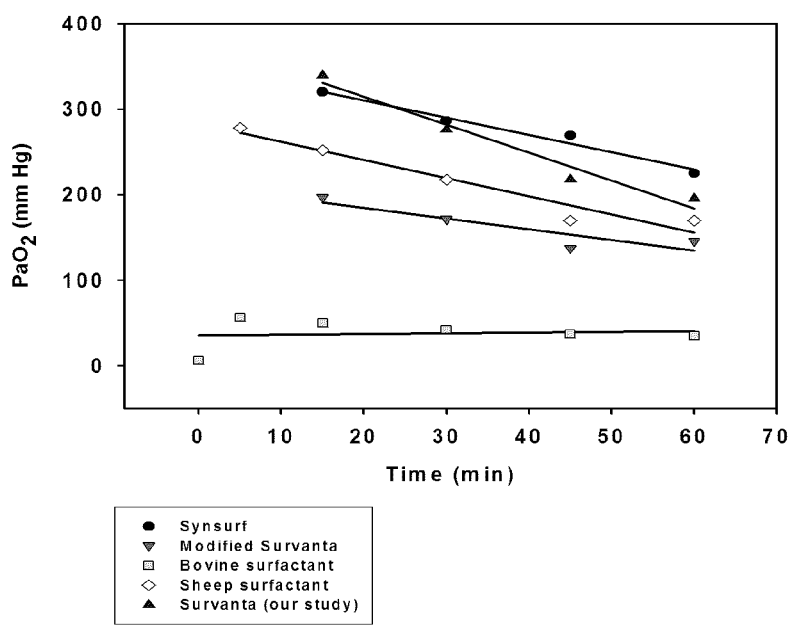
FIG. 8: is a graph of $PaO_2$ (mm Ng) versus Time (min) showing a comparison of oxygenation between the composition of the disclosure, modified Survanta®, Bovine Survanta®; sheep pulmonary surfactant, Survanta® (this study)
Figure 9:
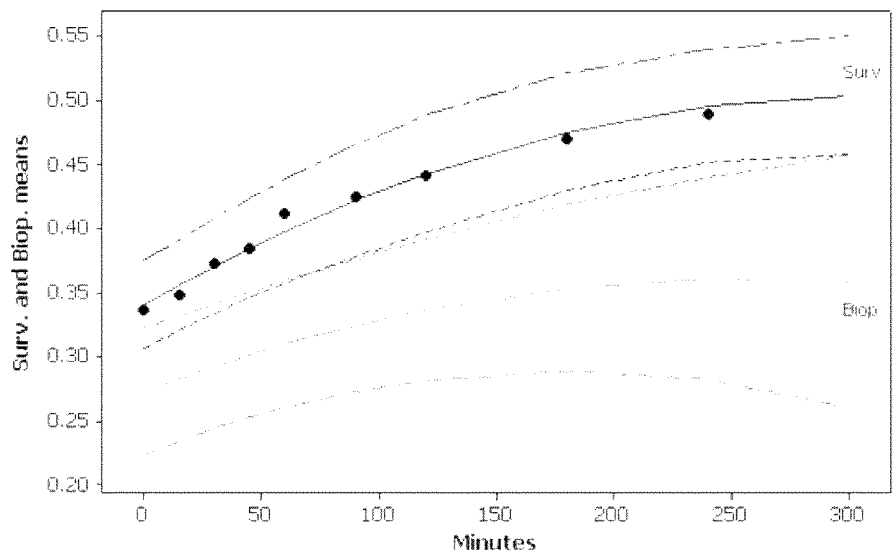
FIG. 9: is a graph of the composition of the disclosure and Survanta® mean dynamic respiratory compliance data versus Time (min) showing the observed means and means of fitted curves of n=6 lambs treated with the present composition and Survanta®, as described in Example 3.

FIG. 6 shows an increase in respiratory compliance over time in the animals in both groups. Interestingly, in both groups, uncoupling between oxygenation (FIG. 4, decrease) and dynamic respiratory compliance (FIG. 6, increase) took place. This negative correlation is shown in FIG. 7. A comparison of these results with findings reported in literature is shown in FIG. 8. Additional statistical analysis of the changes in dynamic respiratory compliance, set out in more detail hereafter, showed that there is an indication of a difference between Survanta and Synsurf (FIG. 9). Over the time interval approximately 90 to 300 min, the lower limit for Survanta lies slightly above the upper limit for Synsurf.

At the end of the study, the phosphatidylcholine in bronchoalveolar lavage (BAL) fluid of both Survanta®- and Synsurf treated animals consisted mainly of C16:0 (palmitic acid). BAL fluid of Synsurf-treated animals differed from Survanta-treated animals in fatty acid composition in that it contained significantly more palmitic acid (C16:0) and oleic acids (C18:1), whilst containing significantly less stearic (C18:0), myristic (C14:0) and pamitoleic acids (C16:1) (Table 6). In so far that palmitic acid (C16:0) is essential for lowering surface tension, there was no correlation between Cdyn and C16:0, nor between Cdyn and BAL fluid phosphatidylcholine (µg phospholipid/µg protein) (data not shown).

TABLE 6

Fatty acid composition of bronchoalveolar fluid phosphatidylcholine at the end of the study. Fatty acid distribution-percent of total fatty acids (Mean % SD)

| Fatty acid | Survanta ® | Synsurf | P-value |
|---|---|---|---|
| C 14:0 | 4.9 (0.5) | 1.0 (0.48) | <0.05 |
| C 16:0 | 82.8 (1.5) | 96.1 (1.4) | <0.05 |
| C 16:1 | 2.9 (0.32) | 0.89 (0.34) | <0.05 |
| C 18:0 | 1.9 (0.62) | 0.47 (0.22) | <0.05 |
| C 18:1 | 0.57 (0.1) | 1.31 (0.61) | <0.05 |

Representative lung histology sections of lambs treated with Survanta® or Synsurf did not differ significantly (data not shown). No morphometric differences existed between the Synsurf and Survanta® groups for alveolar size (p=0.3) or alveolar volume (p=0.29) (Table 7).

TABLE 7

Morphometric parameters

| | Septal Thickness (µm) Mean ± SD | Linear intercept (µm) Mean ± SD | Alveolar Volume (µm) Mean ± SD |
|---|---|---|---|
| Synsurf | 5.04 (0.27) | 43.03 (2.52) | 8.42 (1.51) |
| Survanta | 5.36 (0.60) | 44.59 (4.91) | 9.57 (3.23) |

After pulmonary surfactant instillation, the peripheral total white blood cell count (WCC) of the Synsurf-treated lambs decreased significantly in comparison to the pre-treatment level (p=0.01). Post treatment WCC levels were significantly lower in the Synsurf-treated group in comparison that of the Survanta®-treated lambs (p=0.01). However, no differences were evident in the inflammatory cell infiltrates in the lung (histology) between the different pulmonary surfactant treated groups.

Discussion

After early rescue treatment of pulmonary surfactant-deficiency in premature lambs, Synsurf and Survanta® were indistinguishable based on gas exchange, dynamic respiratory compliance and lung histology. We reason that deterioration in blood gas measurements could partly be as a result of pulmonary surfactant inhibition by plasma protein leakage into the airways (previously shown by others), compounded by uneven spread of pulmonary surfactant when instilled as rescue therapy, or inhibitory action of oxyradicals on pulmonary surfactants (ventilated for 5 hours with 100% oxygen), all of which worsens intrapulmonary shunting. In this regard, protein leaks across the alveolar epithelium may be decreased by SRT before the first breath/onset of ventilation.

The BAL fluid fatty acid composition at the end of the experiment contained more than the minimum required palmitic acid in phosphatidylcholine for adequate lung function (Shelley et al. 1979). The polymers in the Synsurf formulation may have assisted in in vivo adsorption and spreading of the C16:0 fatty acids to the pulmonary surfactant layer.

Statistical Analyses of Survanta® and Synsurf $PaO_2$ Data

Plotting Survanta® and Synsurf values against time for individual animals shows, in most cases, a downward asymptotic trend with time. Transforming the observed $PaO_2$ values to $\log_e (PaO_2)$ produces observed trends which can be modelled by quadratic curves, except that the observations at Time=0 were are consistently too low to fit the quadratic pattern. In what follows the observations at Time=0 were omitted. A quadratic curve was fitted to the observed $\log_e (PaO_2)$ vs Time (Minutes) data of every animal, yielding 6 Survanta® curves and 6 Synsurf curves. The mean observed Survanta® and Synsurf values were calculated and they are plotted as dots in FIG. 5. The means of the fitted curves were calculated and are shown as smooth curves. At time points 15, 30, etc the standard errors of the mean fitted values were computed: they depend on the between animal variation of the fitted values. The confidence bands shown in FIG. 5 are Mean±1.57 (s.e. Mean). The multiplier 1.57 is chosen such that non-overlapping of the bands indicates a significant difference between Survanta® and Synsurf at level approximately 0.05.

There is no indication of significant difference between Survanta® and Synsurf. The mean fitted curve for Synsurf lies within the confidence bands for Survanta, and vice versa.

Statistical Analyses of Survanta® and Synsurf Dynamic Respiratory Compliance Data Plotting Survanta® and Synsurf values against time for individual animals shows that there is a trend with time. It is not linear but can be represented adequately by a quadratic curve.

A quadratic curve was fitted to the data of every animal, thus 6 Survanta® curves and 6 Synsurf curves. The mean observed Survanta® and Synsurf values were calculated and they are plotted as dots in FIG. 9. The means of the fitted curves were calculated and are shown as smooth curves in FIG. 9. At time points 0, 15, 30, etc the standard errors of the mean fitted values were computed: they depend on the between animal variation of the fitted values. The confidence bands shown in FIG. 9 are Mean±1.57 (s.e. Mean). The multiplier 1.57 is chosen such that non-overlapping of the bands indicates a significant difference between Survanta® and Synsurf at level approximately 0.05.

Over time interval approximately 90 to 300 the lower limit for Survanta® lies above the upper limit for Synsurf.

Example 4: Pulmonary Surfactant Treatment for Respiratory Distress Syndrome: A Study in Preterm Lambs A randomized trial was carried out in which systemic oxygenation and lung mechanics during instillation of Saline (control), Synsurf or porcine-derived pulmonary surfactant Curosurf® (Chiesi, Safeline Pharmaceuticals) was analysed before first breath in preterm lambs.

Methods

Pulmonary Surfactants Used

Synsurf prepared according to the procedure set out in Example 1.

Curosurf®

Determination of In Vivo Pulmonary Surfactant Activity

Eighteen pregnant Dohne-Merino ewes were preanesthetized, intubated and received halothane anesthesia and intermittent positive pressure ventilation. A cesarean section was performed on the time-dated pregnant ewes at 129-130 days gestational age (normal gestation 150 days). The fetal head was exposed, a tracheotomy performed and an uncuffed 4.5 mm endotracheal tube placed. Ten to 20 ml of fetal lung fluid was sampled to determine lung maturity. The umbilical cord was cut; animals were then delivered, dried, and weighed, sedated and paralyzed. Pulmonary surfactant was administered before first breath. To minimalise lung damage an expiratory tidal volume of 6-8 ml/kg was used for the first 30 min. Expiratory tidal volume (Vte) was then increased to 8-10 ml/kg. Hereafter ventilator settings were then held constant throughout the study at a fractional concentration of inspired oxygen ($FiO_2$) of 1.0, rate 40 bpm, Ti 0.70 sec and PEEP 4 cm $H_2O$. Lambs were assigned into one of three groups (n=6 lambs/group). The two pulmonary surfactants were tested (concentration 100 mg/kg): Group A received Synsurf and Group B, Curosurf® and the control group equivalent volumes of saline. The measurements of physiological variables (blood pressure, heart rate, rectal temperature and when possible, pulmonary artery pressure), blood gases and in vivo lung mechanics were taken at 30, 45, 60, 90, 120, 180, 240 and 300 min after SR. After 5 hours, all live animals were killed. The chest wall was opened and quasi-static maximal inspiratory capacity (MIC) of the intact lung at 35 cm$H_2O$ peak plateau pressure (zero PEEP) was determined after exsanguination. Photographs of the macroscopic appearance of the anterior and posterior aspects of excised lungs were taken and the lung injury patterns categorized according to photographs: (a) normal appearance, (b) 'typical' distribution of mild injury pattern, (c) 'typical' distribution of mild-moderate injury pattern, and (d) severe injury pattern. The left main bronchus was ligated and the left caudal lobe removed for lung/water content measurements, i.e. wet-to-dry [w/d] ratio and lung wet-dry-to-wet ratio [fraction of wet weight]. In lambs without a pneumothorax, the remaining lung (right lung caudal, middle and cranial lobes) was then gravitationally filled with formaldehyde 4% and inflated under a constant pressure of 25 cm$H_2O$. This lung was used for histology and morphometry.

Results

A total of 18 lambs were studied. Table 8 gives an overall summary of the pre-treatment parameters for the three groups. All the lambs were severely pulmonary surfactant deficient, as their lecithin:sphingomyelin (L/S) ratio was less than 2 and the lamellar body counts less than 15 000 per µL (mean 5278). The pulmonary surfactant deficiency was further reflected in the overall low mean dynamic compliance of the respiratory system (Cdyn) (0.31±0.09 ml/cm$H_2O$/kg) and poor oxygenation status as reflected by a low a/A ratio (0.03±0.01) and high OI (53.68±32.10).

TABLE 8

| | Physiological Variables at time 0 Parameters (Mean ± SD) | | | |
|---|---|---|---|---|
| VARIABLE | ALL (n = 18) | SALINE (n = 6) | SYNSURF ® (n = 6) | CUROSURF ® (n = 6) |
| L/S ratio | 1.040 (0.12) | 1.144 (0.1) | 0.973 (0.1) | 0.973 (0.05) |
| $PaO_2/FiO_2$ | 25.19 ± 9.42 | 29.4 ± 7.56 | 27.63 ± 9.3 | 19.25 ± 9.18 |
| $PaCO_2$ (kPa) | 6.28 ± 1.27 | 6.77 ± 1.04 | 5.84 ± 1.22 | 6.31 ± 1.53 |
| $CO_2$ total (mmol/l) | 26.75 ± 2.97 | 26.76 ± 2.86 | 26.57 ± 4.39 | 26.92 ± 1.53 |
| Cdyn (ml/cm$H_2O$/kg) | 0.31 ± .09 | 0.38 ± 0.12 | 0.27 ± 0.06 | 0.31 ± 0.05 |
| a/A Ratio | 0.03 ± 0.01 | 0.04 ± 0.01 | 0.04 ± 0.02 | 0.03 ± 0.01 |
| OXYGENATION STATUS (cm $H_2O$/mmHg) | 53.68 ± (32.10) | 43.11 (15.16) | 44.06 (14.75) | 73.89 (48.18) |
| Vte/kg | 7.09 ± 1.13 | 6.78 ± 1.67 | 7.17 ± 0.85 | 7.28 ± 0.97 |
| pH | 7.35 ± 0.08 | 7.31 ± 0.06 | 7.39 ± 0.07 | 7.34 ± 0.10 |

No statistical differences were found for the different parameters listed in the table.

Initial Response to Treatment

Figure 10:
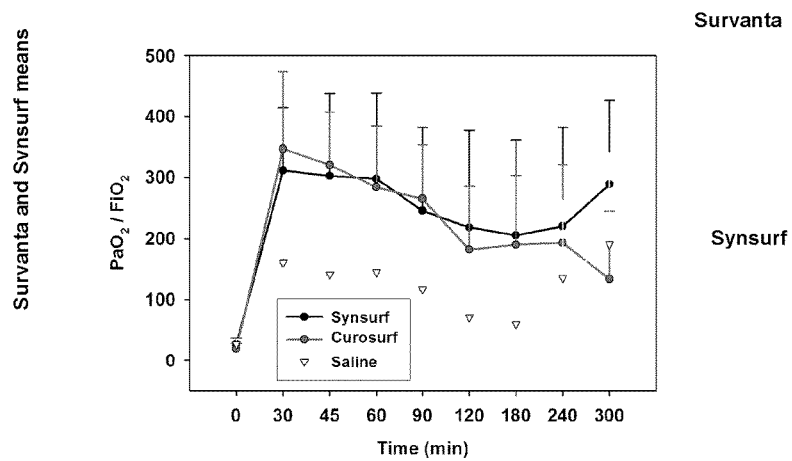
FIG. 10: is a graph of $Pa_2/FiO_2$ over Time (min) showing the oxygenation profile of lambs treated with the composition of the disclosure, Curosurf or saline as described in Example 3.
Figure 11:
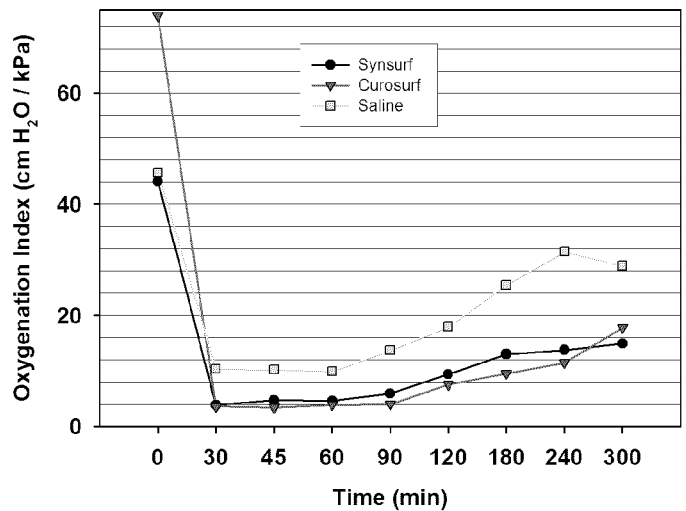
FIG. 11: is a graph of the oxygenation index (cm $H_2O$/kPa) over Time (min) of lambs treated with the composition of the disclosure, Curosurf®, or saline as described in Example 3.

After instillation of vehicle, all three groups experienced an improvement in oxygenation status within 30 minutes (FIG. 10, FIG. 11). Although there were no significant differences between the $PaO_2/FiO_2$ ratios of the Curosurf®-treated and Synsurf-treated lambs at time-point 30-minutes, in comparison to the saline-treated group, only the Synsurf-treated group had a significantly higher $PaO_2/FiO_2$ ratio (p=0.03). At time-point 45 minutes, Synsurf-treated animals had reached a significantly higher $PaO_2/FiO_2$ ratio compared to lambs treated with Saline (p=0.046). Animals that received pulmonary surfactant had a significantly improved oxygenation status between 30 minutes and 240 minutes, above that of the animals treated with saline (FIG. 10, FIG. 11). Although Curosurf-treated animals experienced a significantly improved oxygenation status between the start of the experiment and time-point 300 minutes (p=0.046), their mean $PaO_2/FiO_2$ ratio decreased significantly over time between the 30-minute and 300-minute time-point (p=0.046). At 300 minutes, Synsurf-treated lambs had a higher, $PaO_2/FiO_2$ ratio and a/A ratio when compared to their 30-minute time-point. At the 300-minute time-point, Synsurf-treated lambs had significantly better $PaO_2/FiO_2$ (vs Curosurf®, p=0.046; vs Saline, p=0.043) and a/A ratios (vs Curosurf®, p=0.046; vs Saline p=0.043) compared to that of lambs treated with Curosurf® or Saline. At 300 minutes, Synsurf-treated lambs had a similar oxygenation status to that of Curosurf®-treated lambs, but a lower oxygenation status compared to Saline-treated lambs (p=0.345) (Table 9, FIG. 10, FIG. 11).

TABLE 9

Physiological Variables at time 300 min (end of study)- Parameters (Mean ± SD)

| VARIABLE | ALL (n = 18) | SALINE (n = 6) | SYNSURF (n = 6) | CUROSURF ® (n = 6) |
|---|---|---|---|---|
| $PaO_2/FiO_2$ | 205.31 ± 141.06 | 190.90 ± 149.58 | 288.88 ± 137.13 | 133.75 ± 110.64 |
| $PaCO_2$ (kPa) | 7.60 ± 2.79 | 7.25 ± 3.14 | 7.03 ± 3.32 | 8.47 ± 2.16 |
| $CO_2$ total (mmol/l) | 25.76 ± 2.85 | 24.00 ± 2.50 | 26.20 ± 2.25 | 26.78 ± 3.34 |
| Cdyn (ml $H_2O$/kg) | 0.46 ± .07 | 0.47 ± 0.07 | 0.45 ± 0.09 | 0.48 ± 0.05 |
| a/A Ratio | 0.29 ± 0.2 | 0.27 ± 0.21 | 0.40 ± 0.21 | 0.21 ± 0.16 |
| OXYGENATION STATUS (cm $H_2O$/mmHg) | 20.54 (27.72) | 28.96 (36.06) | 14.89 (30.03) | 17.77 (16.65) |
| Vte/kg | 9.09 ± 1.14 | 9.46 ± 0.65 | 8.45 ± 1.13 | 9.43 ± 1.33 |
| pH | 7.25 ± 0.15 | 7.25 ± 0.20 | 7.31 ± 0.15 | 7.20 ± 0.11 |

Figure 12:
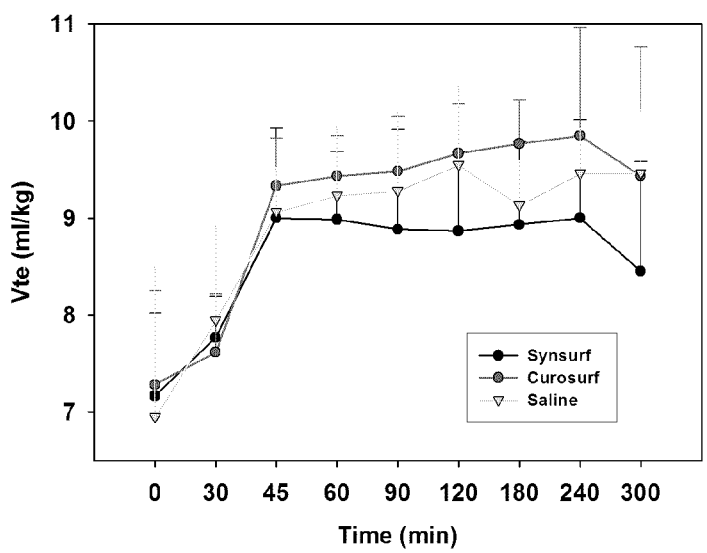
FIG. 12: is a graph of the tidal volume (Vte) (ml/kg) over Time (min) of lambs treated with the composition of the disclosure, Curosurf®, or saline as described in Example 3.
Figure 13:
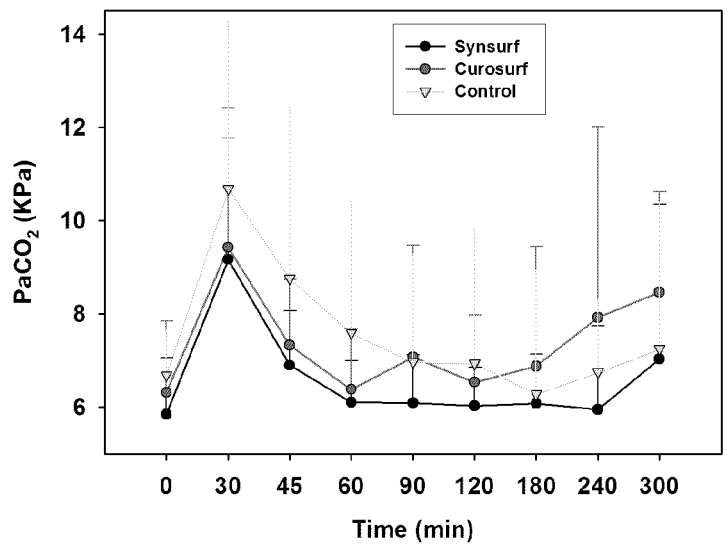
FIG. 13: is a graph of the of the arterial carbon dioxide tension ($PaCO_2$) over time, showing the profile of the $PaCO_2$ of lambs treated with the composition of the disclosure, Curosurf® or saline as described in Example 3.

Except at time 180 and 300 min, respectively, where Synsurf-treated lambs had significant lower expiratory tidal volumes (vs Curosurf, p=0.028; vs Saline, p=0.043), there were no differences between the groups (FIG. 12). Arterial $PaCO_2$ values (FIG. 13) between the start of the study and 300 minutes showed no significant difference and mean arterial blood pressure was within normal limits for all animals during the study period (mean 55.8±7.3).

Figure 14:
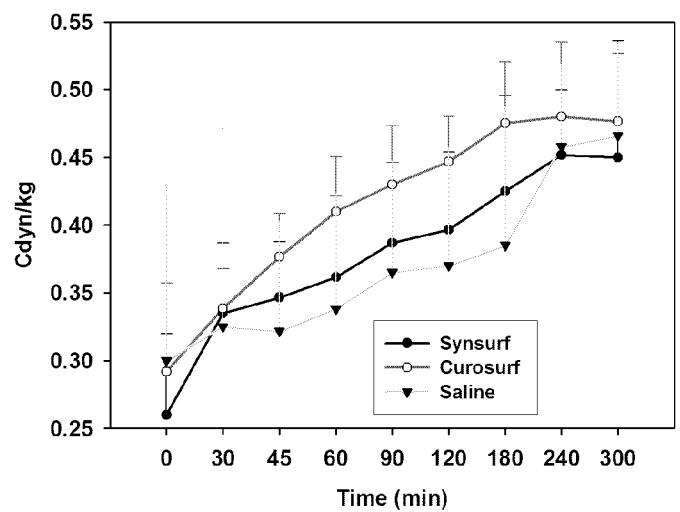
FIG. 14: is a graph of the dynamic respiratory compliance (cdyn/kg) over Time (min) in lambs treated with the composition of the disclosure, Curosurf® or saline as described in Example 3.

Total dynamic respiratory compliance (Cdyn) (FIG. 14) steadily increased in all of the groups over time, yet only in the pulmonary surfactant-treated groups was the increase significant between time-point 0 (start of experiment) and 300 minutes (p=0.0012 and p=0.00026, for Synsurf and Curosurf®, respectively). There were no significant inter-group differences for Cdyn between the start of the experiment and 300 minutes.

The cord blood had the typical lymphocytosis of fetal blood for all study groups (Table 10). After 5 hours of ventilation, the numbers of white blood cells changed significantly only in the Curosurf®-treatment group. In this group, the mean peripheral white blood cell count (WCC) rose from 1.2 to 3.0 (p=0.02). In all of the groups the predominant shift from a lymphocytosis in cord blood to a neutrophilic predominance occurred after 5 hours of ventilation. There were, however, no significant differences between the groups.

TABLE 10

White blood cell count and differential count at birth and after 5 h of ventilation of preterm lambs

|  | Synsurf | Curosurf ® | Saline |
|---|---|---|---|
| Baseline Count |  |  |  |
| WBC × $10^9$/l | 1.9 (1.3) | 1.2 (0.8) | 3.1 (2.6) |
| Neutrophils % | 20.3 (15.2) | 23.6 (27.9) | 19.7 (23.4) |
| Lymphocytes End of Study | 65.9 (12.6) | 65.9 (21.1) | 72.6 (23.1) |
| WBC × $10^9$/l | 1.8 (1.7) | 3.0 (1.9) | 2.4 (1.3) |
| Neutrophils % | 42.8 (38.7) | 53.4 (24.1) | 45.4 (31.4) |
| Lymphocytes | 53.6 (35.5) | 38.5 (22.6) | 49.8 (32.3) |

All of the animals in the pulmonary surfactant treated groups survived. Two animals developed a pneumothorax during the study, one each in the saline group and Synsurf-treated group, respectively. One animal in the Saline-treated group died prior to the 300-minute mark.

Quasi-static lung volume measurements, maximal inspiratory capacity (MIC), as determined in the open-chest state, were 36.22±10.21 ml/kg for Saline-treated, 33.95±8.03 ml/kg for Curosurf®-treated, and 32.96±1.98 ml/kg for Synsurf treated lambs, which were not different from one another (p=ns). The macroscopic appearance of the lungs of 16 lambs (lungs of 2 lambs in the Saline-treated group were not available) was categorized (data not shown). The appearance of lungs of the majority of lambs (n=8) was classified under the mild-moderate injury pattern and severe injury pattern (n=5). Only in 2 lambs were the lungs of 'normal appearance', one lamb in the Saline, and one lamb in the Curosurf®-treated groups, respectively. One lamb in the Synsurf-group had a mild injury pattern. There were no clear visible group-differences in regard to the distribution of the injury patterns.

Table 11 shows the calculations for postmortem lung water content as reflected by w/d and w/d/w ratios. No significant differences were observed in the fraction of wet lung weight, expressed in the w/d/w ratio between the three groups. Likewise, dry lung weight, expressed as the w/d ratio, showed no significant difference between any of the groups.

TABLE 11

Lung wet-to-dry (W/D) ratio and lung wet-to-dry-to-wet (W/D/W) ratio. Mean ± SD

|  | W/D Ratio Mean ± SD | W/D/W Ratio Mean ± SD |
|---|---|---|
| Synsurf | 6.2 (0.65) | 0.40 (0.11) |
| Curosurf® | 5.67 (1.12) | 0.38 (0.08) |
| Saline | 6.49 (1.57) | 0.38 (0.16) |

Discussion

A controlled trial was conducted to compare systemic oxygenation and lung mechanics in pulmonary surfactant-deficient preterm lambs after instillation of Saline (control), Synsurf or porcine-derived pulmonary surfactant Curosurf®, before first breath. Treatment with pulmonary surfactants produced clear differences in oxygenation status, but not dynamic respiratory compliance. Over the study period pulmonary surfactant replacement with Synsurf resulted in a more sustained improved oxygenation response compared to that of Curosurf® or Saline-treated animals.

Although dynamic respiratory compliance increased significantly only in the pulmonary surfactant treated groups, their time profiles did not differ significantly from that of saline-treated animals. As per Example 2, an increase was again observed in compliance in relation to a concurrent decrease in oxygenation over time, but this time, only in the Curosurf® and saline-treated groups. An 'uncoupling' or divergence between oxygenation and compliance was not recorded in the Synsurf group as observed in Example 2, where pulmonary surfactant was administered as rescue treatment.

The in vivo efficacy of a synthetic pulmonary surfactant preparation has been demonstrated herein in animal model studies. Although the precise mechanisms by which Synsurf affects the duration and extent of the oxygenation response in the animals remains to be clarified, we suggest that the amphiphilic-like character (Kurutz & Lee. 2002; Lipp. et al. 1996; Baatz et al. 1990) of the simple polymer complex might be the key to mimic the much needed function of SP-B.

Example 5: Pulmonary Surfactant as a Permeability Enhancer of Drugs Through Tissues The role of the surfactant composition of this disclosure in the permeability of chemical agents/drugs and peptides through porcine lung, artery, buccal mucosa and human vaginal mucosa was investigated.

Methods
Pulmonary Surfactants Used
Synsurf (Novel Synthetic Pulmonary Surfactant)
Generic Exosurf (prepared by a standard method)
Curosurf® (Porcine derived pulmonary surfactant)
Survanta® (Bovine derived pulmonary surfactant)
Materials The study was approved by the Committee for Human Research of the Faculty of Health Sciences, University of Stellenbosch. Porcine lung and buccal mucosa were obtained from the animal house. Vaginal mucosa was obtained from postmenopausal patients following vaginal hysterectomies. Specimens were placed in either phosphate buffered saline (PBS) or Eagle's Minimum Essential Medium (MEM) without L-glutamine and $NaHCO_3$ and transported to laboratory. Specimens were snap-frozen in liquid nitrogen and stored at −85° C. for 6 months.

Drugs/peptides/chemical compounds differing widely in molecular size and lipophilicity used in permeation studies were:

$^3$H-17β-estradiol (Mw=272 Da). This drug is used for hormone replacement therapy during the female climacteric.

$^3$H-reduced arecoline (Mw=141 Da). This alkaloid has the potential to cause oral cancer as well as submucous fibrosis.

$^3$H-Hydrocortisone (Mw=362.4 Da). This is a naturally occurring corticosteroid used principally for its anti-inflammatory and immunosuppressive actions, or for hormone replacement therapy.

$^3$H-Dexamethasone (Mw=392.5 Da). This is one of the potent synthetic analogues of cortisol used for the prevention and treatment of cerebral oedema and it is the drug of choice for suppression of ACTH production.

$^3$H-Vasopressin (Mw=1084 Da). This is the antidiuretic peptide hormone important for its actions on the kidney.

FITC-labelled MDY-19 (Mw=2409.5 Da) a carrier peptide, and FITC-labelled MEA-5 (Mw=2911.4 Da), a microbicidal peptide.

Enhancers to improve permeability were Dipalmitoyl-phosphatidylcholine (DPPC)-based pulmonary surfactants. Synsurf and Exosurf were prepared as described in Example 1, while Curosurf® and Survanta® were purchased.

Diffusion Kinetics Apparatus

Diffusion kinetics through porcine lung and buccal mucosa, as well as human vaginal mucosa were determined by using a continuous flow-through diffusion system.

Tissue specimens of different mucosa were trimmed and seven disks (±4 mm) were mounted in the flow-through diffusion cells (exposed area 0.039 cm$^2$). Prior to commencement of the experiment, tissue disks were equilibrated for 10 min with PBS, pH 7.4 at 20° C. in both the donor and acceptor compartments of the diffusion cells. Following equilibration, the PBS was removed from the donor compartment and replaced with 1 ml of tritiated compound/peptide (0.1-1.4 µCi). Aliquots (100 µl) were removed within minutes from each of the seven donor compartments for determination of donor cell concentration at time-zero ($C_0$). PBS (pH 7.4) was pumped through acceptor chambers at a rate of 1.5 ml/h. Fractions were collected at 2 h intervals for 48 h. Scintillation cocktail (10 ml) was added to each sample collected and counted in a liquid scintillation counter until a 2-s value of 1% was reached. Quenching for each sample was automatically corrected in the counter. Flux (J) values across membranes were calculated by means of the relationship: $J=Q/A \cdot t$ (dpm·cm$^{-2}$·min$^{-1}$), where Q=quantity of substance crossing the membrane (dpm). A=membrane area exposed (cm$^2$) and t=time of exposure (min). Peptides were determined by fluorescence spectrometry.

Steady state kinetics: When no statistical significant differences ($p<0.05$) (ANOVA & Duncan's multiple range test) between flux values were obtained over at least 2 consecutive time intervals, a steady state (equilibrium kinetics) was assumed to have been reached for a particular specimen.

Statistical analysis: An unpaired t test with Welch's correction was used to investigate possible differences between flux means at 2-h intervals A significance level of $p<0.05$ was used. Comparison of whole curves was done by using the F-test.

Results

Figure 15:
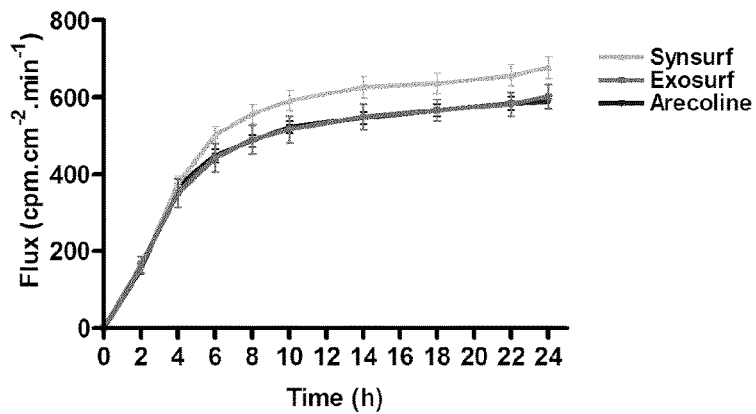
FIG. 15: is a graph showing the mean flux values of arecoline in the presence of the composition of the disclosure and Exosurf® across porcine lung tissue.

Synsurf enhanced the flux rate of arecoline across porcine lung tissue when compared to Exosurf (FIG. 15). The p value for Synsurf/Arecoline was p=3.75311 $E^{-11}$, while that for Exosurf/Arecoline was p=0.9554. The n-value for Synsurf was 31; for Exosurf was 17; and for Arecoline was 33.

Figure 16:
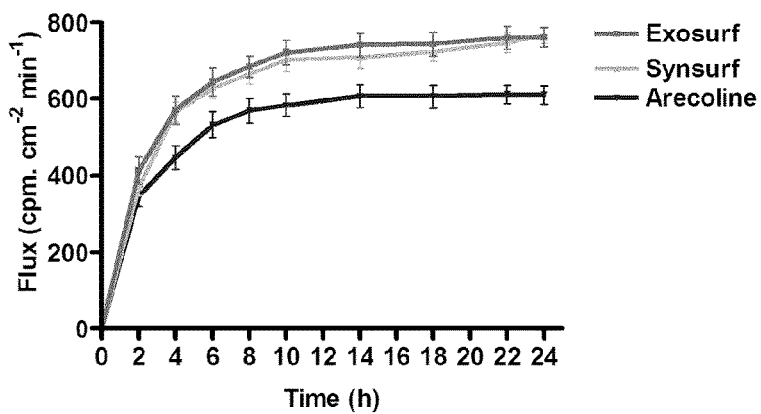
FIG. 16: is a graph showing the mean flux values of arecoline in the presence of the composition of the disclosure and Exosurf® across human vaginal mucosa tissue.

Both Synsurf and Exosurf enhanced the flux rate of arecoline across human vaginal mucosa (FIG. 16). Differences between Synsurf and Exosurf values were non-significant. The p value for Synsurf Arecoline was p=1.0388 $E^{-5}$; for Exosurf/Arecoline was p=1.807 $E^{-14}$; and for Synsurf/Exosurf wasp=0.74029. the n-value for Synsurf was 18; for Exosurf was 17; and for Arecoline was 7.

Figure 17:
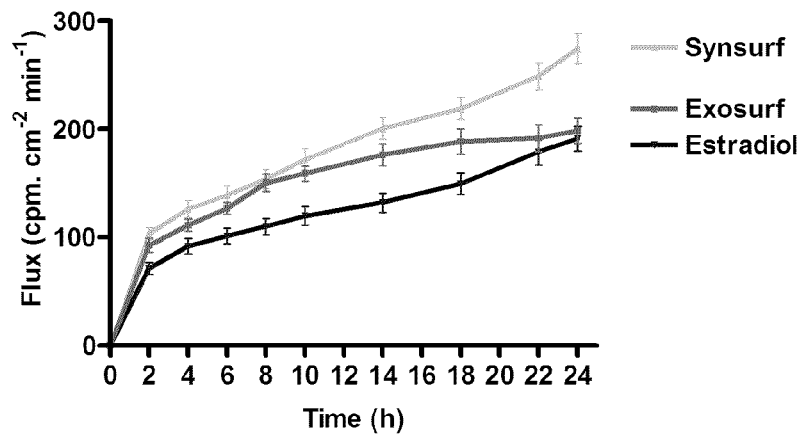
FIG. 17: is a graph showing the mean flux values of estradiol in the presence of the composition of the disclosure and Exosurf® across porcine lung tissue.

Both Synsurf and Exosurf enhanced the flux rate of estradiol across porcine lung tissue (FIG. 17). However, enhancement with Synsurf was much greater. The p value for Synsurf/Estradiol was p=4.51 $E^{-26}$; for Exosurf/Estradiol was p=8.9 $E^{-10}$; and for Synsurf/Exosurf was p=1.3 $E^{-9}$. The n-value for Synsurf was 24; for Exosurf was 13; and for Estradiol was 15.

Figure 18:
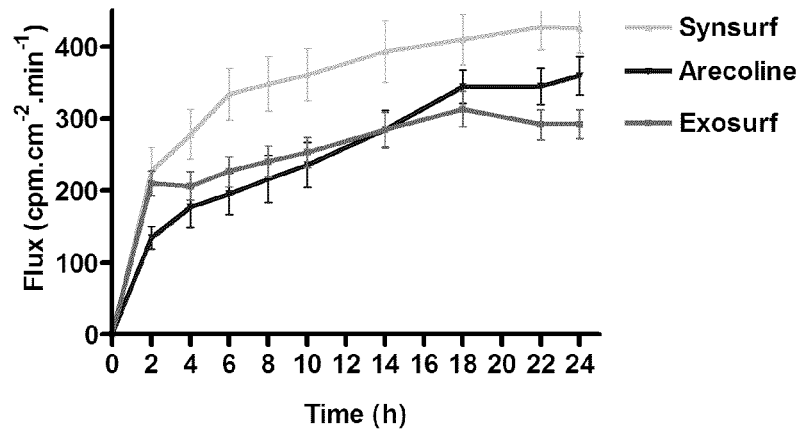
FIG. 18: is a graph showing the mean flux values of arecoline in the presence of the composition of the disclosure and Exosurf® across porcine buccal mucosa tissue.

Synsurf enhances the flux rate of arecoline across porcine buccal mucosa when compared to Exosurf (FIG. 18). The p-value for Synsurf/Arecoline was p=5.58 $E^{-10}$; for Synsurf/Exosurf was p=3.5 $E^{-12}$; and for Exosurf/Arecoline was p=0.1355. The n value for Synsurf was 11; for Exosurf was 17; and for Arecoline was 12.

Figure 19:
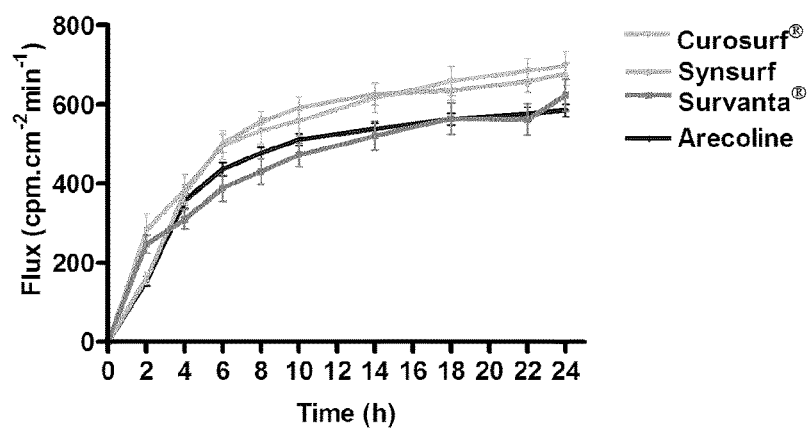
FIG. 19: is a graph showing the mean flux values of arecoline in the presence of the composition of the disclosure, Curosurf®, and Survanta® across porcine lung tissue.

Both Synsurf and Curosurf® enhanced the flux rate of arecoline across porcine lung tissue (no statistical difference), while Survanta® gave no enhancement (statistical non-significant) (FIG. 19). The p-value for Synsurf/Arecoline was p=3.75 $E^{11}$; for Curosurf®/Arecoline was p=1.7 $E^{-10}$; for Survanta®/Arecoline was p=0.1183; and for Synsurf/Curosurf® was p=0.4745. The n-value for Synsurf was 31; for Curosurf® was 17; for Survanta® was 16; and for Arecoline was 33.

Figure 20:
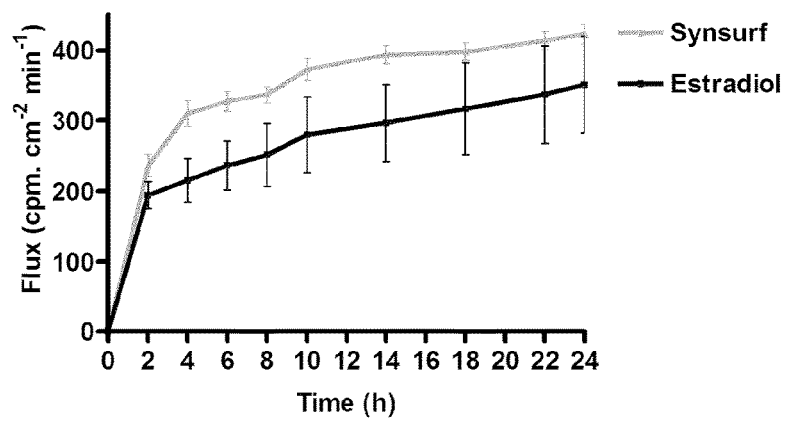
FIG. 20: is a graph showing the mean flux values of estradiol in the presence of the composition of the disclosure across porcine artery lung tissue.

Synsurf enhanced the flux rates of estradiol across porcine lung artery tissue (FIG. 20). The p-value for Synsurf/Estradiol was p=8.15 $E^{-6}$, and the n-value for Synsurf was 14, and for Estradiol was 10.

Figure 21:
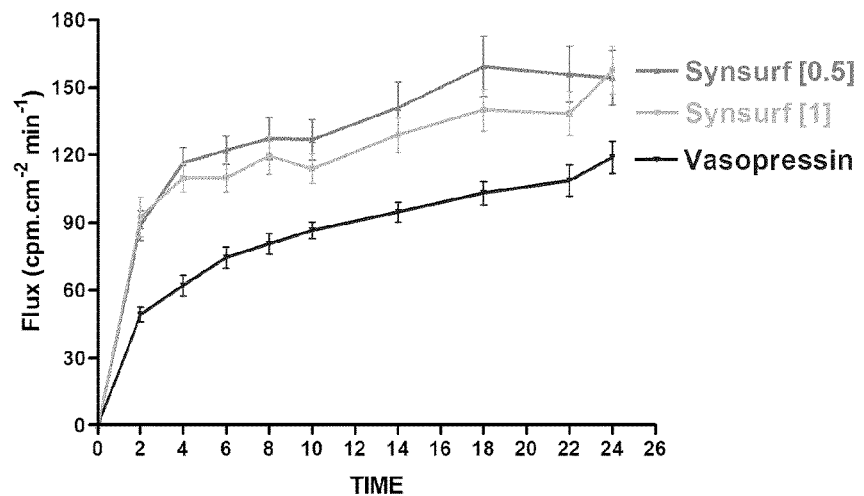
FIG. 21: is a graph showing the mean flux values of vasopressin in the presence of the composition of the disclosure across porcine artery lung tissue.

Both diluted (½ concentration) and undiluted Synsurf enhanced the flux rates of vasopressin across porcine lung tissue (FIG. 21). The p value for Synsurf [1]/Vasopressin was p=2.4 $E^{-25}$; and for Synsurf [0.5]/Vasopressin was p=2.44 $E^{-35}$. The n-value for Synsurf [0.5] was 15; for Synsurf [1] was 18; and for Vasopressin was 26.

Figure 22:
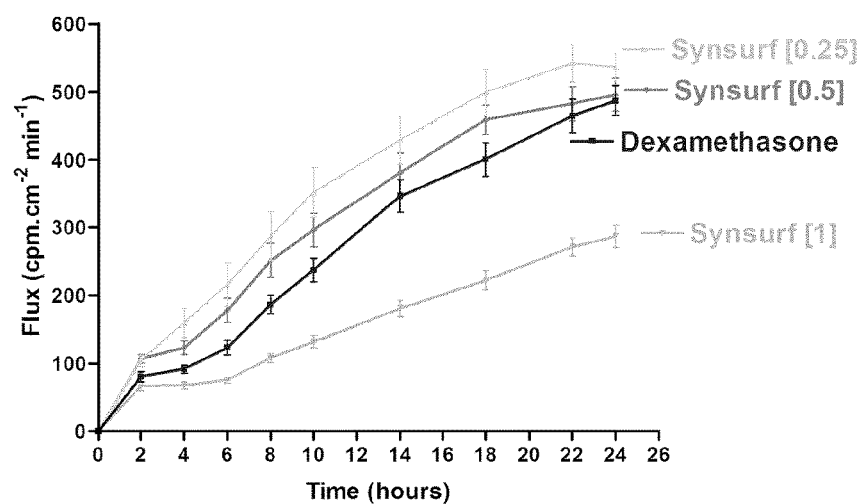
FIG. 22: is a graph showing the mean flux values of dexamethasone in the presence of the composition of the disclosure across porcine lung tissue.

Diluted Synsurf (½ and ¼ concentration) enhanced the flux rates of dexamethasone across porcine lung tissue, while undiluted Synsurf retarded the flux across the lung tissue (FIG. 22). The p-value for Synsurf [0.25]/Dexamethasone was p=2.02 $E^{-11}$; for Synsurf [0.5]/Dexamethasone was p=0.00014. The n-value for Synsurf [0.25] was 20; for Synsurf [0.5] was 18; for Dexamethasone was 22; and for Synsurf [1] was 21.

Figure 23:
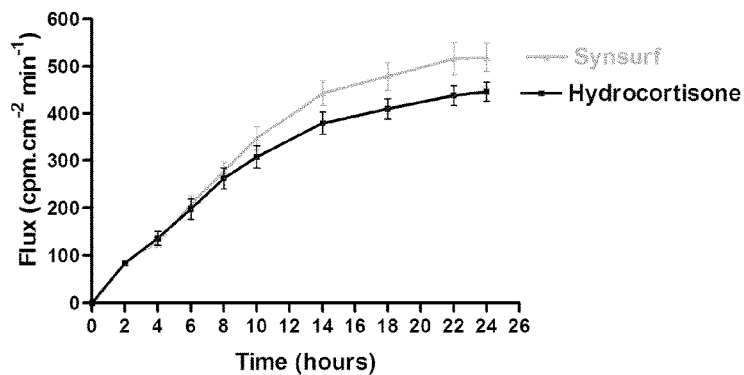
FIG. 23: is a graph showing the mean flux values of hydrocortisone in the presence of the composition of the disclosure across porcine lung tissue.

Synsurf enhanced the flux rate of hydrocortisone statistically significant across porcine lung tissue (FIG. 23). The p value for Synsurf/Hydrocortisone was p=4.37 $E^{-5}$; and the n-value for Synsurf was 24; and for Hydrocortisone was 26.

Figure 24:
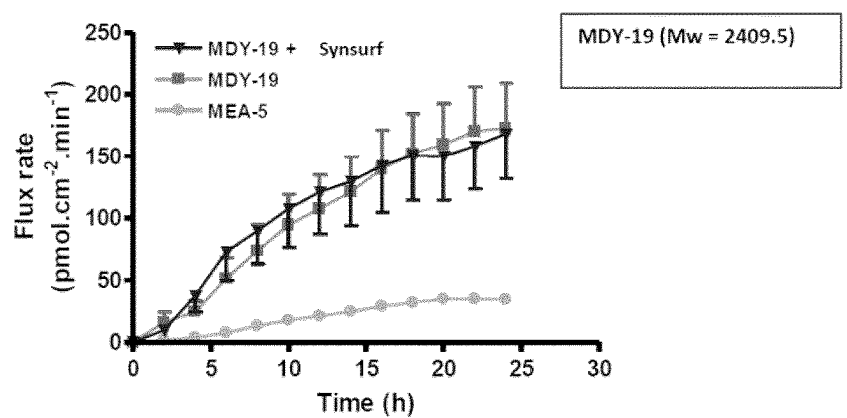
FIG. 24: is a graph showing the mean flux values of FITC-labelled MDY-19 in the presence of the composition of the disclosure across human vaginal mucosa tissue.

Comparison of whole curves showed no statistical enhancement of the carrier peptide MDY-19 with Synsurf (FIG. 24). The p-value for Synsurf+MDY-19 was p=0.1652; and the n-value for MDY-19 was 38; for MEA-5 was 16; and for MDY-19+Synsurf was 20.

Discussion

In these studies, the applicants found that the synthetic DPPC-based pulmonary surfactant Synsurf, enhanced the permeation of chemical compounds/peptides/drugs of different molecular weight (141-2911.4 Da) across lung, buccal, artery and vaginal tissue. Although it's clinical relevance as a permeation enhancer is still to be further investigated, the potential of Synsurf shown in the results above could spawn several new delivery formulations for a wide variety of pharmaceutical agents.

The invention claimed is:

1. A pulmonary surfactant composition having in vivo surface activity and comprising:
    a lipidaceous carrier including a spreading agent for spreading the lipidaceous carrier on an in vivo surface; and
    a peptide complex configured to mimic one or more structural and/or functional properties of natural surfactant proteins comprising poly-L-lysine or a pharmaceutically acceptable salt thereof; and poly-L-glutamic acid or poly-L-aspartic acid or a pharmaceutically acceptable salt thereof;
    wherein the poly-L-lysine or pharmaceutically acceptable salt thereof is present in a range of about 100 to about 135 residues, and poly-L-glutamic acid or poly-L-aspartic acid or a pharmaceutically acceptable salt thereof is present in a range of about 50 to about 86 residues and wherein the peptide complex has a charge-neutralized surface region that interacts with the lipidaceous carrier and a positively-charged surface region that interacts with an aqueous and/or polar environment, the positive charge resulting from an excess of about 14 to about 85 poly-L-lysine or pharmaceutically acceptable salt thereof residues relative to the poly-L-glutamic acid or poly-L-aspartic acid or a pharmaceutically acceptable salt thereof residues, and wherein the ratio of the peptide complex to the lipidaceous carrier is about 3:100 (w/w).

2. A composition according to claim 1, wherein the salt of poly-L-lysine is poly-L-lysine.HBr.

3. A composition according to claim 2, wherein the poly-L-lysine.HBr is of the formula (I) and n ranges from about 100 to about 135

Formula (I)

4. A composition according to claim 3, wherein n ranges from about 103 to about 135.

5. A composition according to claim 3, wherein n ranges from about 103 to about 119.

6. A composition according to claim 1, wherein the salt of poly-L-glutamic acid is poly-L-glutamic acid sodium salt.

7. A composition according to claim 6, wherein the poly-L-glutamic acid sodium salt is of the formula (II) and x is at least 50

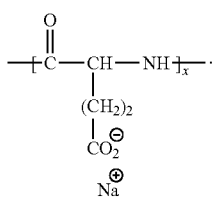

Formula (II)

8. A composition according to claim 7, wherein x is at least 68.

9. A composition according to claim 7, wherein x is at least 86.

10. A composition according to claim 1, wherein the lipidaceous carrier comprises one or more of dipalmitoyl phosphatidylcholine (DPPC), phosphatidylglycerol (PG), hexadecanol, cholesterol, tyloxapol or sodium chloride.

11. A composition according to claim 1, which comprises:
dipalmitoyl phosphatidylcholine (DPPC);
phosphatidylglycerol (PG);
hexadecanol;
tyloxapol;
poly-L-lysine.HBr;
poly-L-glutamic acid sodium salt; and
sodium chloride.

12. A composition according to claim 1, which further comprises a pharmaceutically acceptable carrier.

13. A composition according to claim 1, for treating a condition related to pulmonary surfactant dysfunction or deficiency.

14. A composition according to claim 13, wherein the condition is hyaline membrane disease (HMD), respiratory distress syndrome (RDS), hydrocarbon poisoning, near-drowning, HIV/AIDS-related lung diseases, adult respiratory distress syndrome (ARDS) or acute lung injury (ALI), asthma, chronic obstructive pulmonary disease (COPD), tuberculosis (TB) or severe acute respiratory syndrome (SARS).

15. A composition according to claim 1, which further comprises a pharmaceutical compound or composition for, treating or ameliorating a disease or medical condition.

16. A composition according to claim 1, for increasing the permeability of a pharmaceutical compound or composition across a membrane of a subject.

17. A composition according to claim 15, wherein the pharmaceutical compound or composition is an anti-cancer agent, anti-inflammatory, immunosuppressive agent, antidiuretic agent, carrier peptide, microbicidal peptide, ACTH suppressor, cortisol analogue or hormone replacement therapy agent.

18. A composition according to claim 1, which is suitable for administration to a subject by inhalation, intubation or direct pulmonary administration.

19. A method for preparing a composition according to claim 1, the method comprising the steps of:
mixing dipalmitoyl phosphatidylcholine (DPPC), hexadecanol, and phosphatidylglycerol (PG) in an organic solvent;
removing the organic solvent and obtaining a phospholipid film;
mixing, in an aqueous solution, poly-L-lysine or a pharmaceutically acceptable salt thereof and poly-L-glutamic acid or poly-L-aspartic acid, or a pharmaceutically acceptable salt thereof, and obtaining a peptide complex;
adding the peptide complex to the phospholipid film;
agitating the mixture, and
adding tyloxapol.

20. A method of treating a condition related to pulmonary surfactant dysfunction or deficiency in a subject, which comprises administering to a subject an effective dose of the composition of claim 1.

21. A method according to claim 20, wherein the condition is hyaline membrane disease (HMD), respiratory distress syndrome (RDS), hydrocarbon poisoning, near-drowning, HIV/AIDS-related lung diseases, adult respiratory distress syndrome (ARDS) or acute lung injury (ALI), asthma, chronic obstructive pulmonary disease (COPD), tuberculosis (TB) or severe acute respiratory syndrome (SARS).

22. A method of administering a pharmaceutical compound or composition to a subject, which comprises the step of administering to the subject an effective amount of the pharmaceutical compound or composition together with an effective amount of the composition of claim 1.

* * * * *